(12) United States Patent
Matsuura et al.

(10) Patent No.: US 12,263,044 B2
(45) Date of Patent: Apr. 1, 2025

(54) MEDICAL DISPLAY SYSTEM, CONTROL DEVICE, AND CONTROL METHOD

(71) Applicant: SONY GROUP CORPORATION, Tokyo (JP)

(72) Inventors: Kana Matsuura, Tokyo (JP); Keiichi Yoshioka, Tokyo (JP); Kazuma Takahashi, Tokyo (JP); Shoji Watanabe, Tokyo (JP)

(73) Assignee: SONY GROUP CORPORATION, Tokyo (JP)

( * ) Notice: Subject to any disclaimer, the term of this patent is extended or adjusted under 35 U.S.C. 154(b) by 532 days.

(21) Appl. No.: 17/597,120

(22) PCT Filed: Jul. 3, 2020

(86) PCT No.: PCT/JP2020/026167
§ 371 (c)(1),
(2) Date: Dec. 27, 2021

(87) PCT Pub. No.: WO2021/006201
PCT Pub. Date: Jan. 14, 2021

(65) Prior Publication Data
US 2022/0265384 A1      Aug. 25, 2022

(30) Foreign Application Priority Data

Jul. 5, 2019   (JP) ................................. 2019-126311

(51) Int. Cl.
*G06T 3/40* (2024.01)
*A61B 34/00* (2016.01)
(Continued)

(52) U.S. Cl.
CPC .............. *A61B 90/37* (2016.02); *A61B 34/25* (2016.02); *G06F 3/013* (2013.01); *G06F 3/167* (2013.01);
(Continued)

(58) Field of Classification Search
None
See application file for complete search history.

(56) References Cited

U.S. PATENT DOCUMENTS

| 2012/0189173 A1 | 7/2012 | Markowitz |
| 2014/0171959 A1* | 6/2014 | Yacono ............. G02B 21/0012 606/128 |

(Continued)

FOREIGN PATENT DOCUMENTS

| CN | 110461205 A | 11/2019 |
| EP | 3095378 A1 | 11/2016 |

(Continued)

OTHER PUBLICATIONS

International Search Report and Written Opinion of PCT Application No. PCT/JP2020/026167, issued on Sep. 15, 2020, 09 pages of ISRWO.

*Primary Examiner* — Yanna Wu
(74) *Attorney, Agent, or Firm* — CHIP LAW GROUP

(57) ABSTRACT

There is provided a medical display system that includes a control device including an acquisition unit that acquires an operative field image signal generated by a medical imaging device that images an operative field of a patient and a presented information signal generated by a device that includes an external device excluding the medical imaging device and a control unit that generates a display image on the basis of the operative field image signal and the presented information signal, in which the control unit generates the display image by arranging and displaying presented information generated from the presented information signal in an upper region of a display region of the display image, arranging and displaying an operative field image generated on the basis of the operative field image signal in a middle region that has a length equivalent to the upper region in a horizontal direction, and arranging and displaying user (Continued)

interface information used to control the control device in a region on a lower side of the upper region.

19 Claims, 38 Drawing Sheets

(51) Int. Cl.
  *A61B 90/00* (2016.01)
  *G06F 3/01* (2006.01)
  *G06F 3/16* (2006.01)
  *G06F 3/04842* (2022.01)
(52) U.S. Cl.
  CPC .......... *G06T 3/40* (2013.01); *A61B 2090/378* (2016.02); *G06F 3/04842* (2013.01); *G06F 2203/04803* (2013.01)

(56) References Cited

U.S. PATENT DOCUMENTS

| | | | |
|---|---|---|---|
| 2014/0268060 A1* | 9/2014 | Lee | A61B 3/103 |
| | | | 351/241 |
| 2016/0338570 A1 | 9/2016 | Okusawa et al. | |
| 2018/0260183 A1 | 9/2018 | Ichikawa et al. | |

FOREIGN PATENT DOCUMENTS

| | | | |
|---|---|---|---|
| JP | 2012-228286 A | 11/2012 |
| JP | 2016505312 A | 2/2016 |
| JP | 2017174043 A | 9/2017 |
| JP | 2018-143559 A | 9/2018 |
| JP | 2018-161377 A | 10/2018 |
| WO | 2016/021232 A1 | 2/2016 |
| WO | 2018/179749 A1 | 10/2018 |

* cited by examiner

FIG. 35

A1: Insuff. PRESS 10 mmHg  FLOW 10 L/min  VOL 10 L  NRG  CUT 100 Max W  COAG 100 Max W  BIPOL 100 Max W  TIMER 00:00 20:00

ALERT

TOTAL 3P DURATION 00:00 00

FIG. 36

Camera | Reference | Time Start | Screen | Others

A3

MEDICAL DISPLAY SYSTEM, CONTROL DEVICE, AND CONTROL METHOD

CROSS REFERENCE TO RELATED APPLICATIONS

This application is a U.S. National Phase of International Patent Application No. PCT/JP2020/026167 filed on Jul. 3, 2020, which claims priority benefit of Japanese Patent Application No. JP 2019-126311 filed in the Japan Patent Office on Jul. 5, 2019. Each of the above-referenced applications is hereby incorporated herein by reference in its entirety.

TECHNICAL FIELD

The present technology relates to a medical display system, a control device, and a control method, and more particularly, to a medical display system, a control device, and a control method that can present necessary information without disturbing concentration of an operator.

BACKGROUND ART

An operator who performs an operation while viewing an operative field image captured by a medical imaging device needs to make a decision regarding the operation by viewing information regarding other medical devices other than the operative field image.

Various techniques for easily obtaining the information regarding the plurality of medical devices by the operator have been proposed. For example, Patent Document 1 discloses a technique for aggregating and displaying the operative field image and the information regarding the plurality of medical devices in a single screen.

CITATION LIST

Patent Document

Patent Document 1: Japanese Patent Application Laid-Open No. 2012-228286

SUMMARY OF THE INVENTION

Problems to be Solved by the Invention

In a case where the operative field image and the information regarding the plurality of medical devices are displayed in a single screen, normally, it is required to display the operative field image that is main information to be larger than the information regarding the other medical devices.

Furthermore, it is required for the information regarding the other medical devices not to disturb the concentration of the operator who is viewing the operative field image.

The present technology has been made in consideration of such a situation, and can present necessary information without disturbing the concentration of the operator.

Solutions to Problems

A medical display system according to one aspect of the present technology includes a control device including an acquisition unit that acquires an operative field image signal generated by a medical imaging device that images an operative field of a patient and a presented information signal generated by a device that includes an external device excluding the medical imaging device and a control unit that generates a display image on the basis of the operative field image signal and the presented information signal, in which the control unit generates the display image by arranging and displaying presented information generated from the presented information signal in an upper region of a display region of the display image, arranging and displaying an operative field image generated on the basis of the operative field image signal in a middle region that has a length equivalent to the upper region in a horizontal direction, and arranging and displaying user interface information used to control the control device in a region on a lower side of the upper region.

A control device according to one aspect of the present technology includes an acquisition unit that acquires an operative field image signal generated by a medical imaging device that images an operative field of a patient and a presented information signal generated by a device that includes an external device excluding the medical imaging device and a control unit that generates a display image on the basis of the operative field image signal and the presented information signal, in which the control unit generates the display image by arranging and displaying presented information generated from the presented information signal in an upper region of a display region of the display image, arranging and displaying an operative field image generated on the basis of the operative field image signal in a middle region that has a length equivalent to the upper region in a horizontal direction, and arranging and displaying user interface information used to control the control device in a region on a lower side of the upper region.

A control method according to one aspect of the present technology by a control device, includes acquiring an operative field image signal generated by a medical imaging device that images an operative field of a patient and a presented information signal generated by a device that includes an external device excluding the medical imaging device, generating a display image on the basis of the operative field image signal and the presented information signal, and generating the display image by arranging and displaying presented information generated from the presented information signal in an upper region of a display region of the display image, arranging and displaying an operative field image generated on the basis of the operative field image signal in a middle region that has a length equivalent to the upper region in a horizontal direction, and arranging and displaying user interface information used to control the control device in a region on a lower side of the upper region.

An image processing system according to one aspect of the present technology acquires an operative field image signal generated by a medical imaging device that images an operative field of a patient and a presented information signal generated by a device that includes an external device excluding the medical imaging device, generates a display image on the basis of the operative field image signal and the presented information signal, and generates the display image by arranging and displaying presented information generated from the presented information signal in an upper region of a display region of the display image, arranging and displaying an operative field image generated on the basis of the operative field image signal in a middle region that has a length equivalent to the upper region in a horizontal direction, and arranging and displaying user interface information used to control the control device in a region on a lower side of the upper region.

A control device according to one aspect of the present technology acquires an operative field image signal generated by a medical imaging device that images an operative field of a patient and a presented information signal generated by a device that includes an external device excluding the medical imaging device, generates a display image on the basis of the operative field image signal and the presented information signal, and generates the display image by arranging and displaying presented information generated from the presented information signal in an upper region of a display region of the display image, arranging and displaying an operative field image generated on the basis of the operative field image signal in a middle region that has a length equivalent to the upper region in a horizontal direction, and arranging and displaying user interface information used to control the control device in a region on a lower side of the upper region.

BRIEF DESCRIPTION OF DRAWINGS

FIG. 35 is an enlarged view illustrating the presented information region.

FIG. 36 is an enlarged view illustrating the operation menu region.

MODE FOR CARRYING OUT THE INVENTION

Hereinafter, modes for carrying out the present technology will be described. The description will be made in the following order.

1. First Embodiment
2. Second Embodiment
3. Third Embodiment
4. Fourth Embodiment
5. Modification

1. First Embodiment

Description of Outline of Medical Display System

Figure 1:
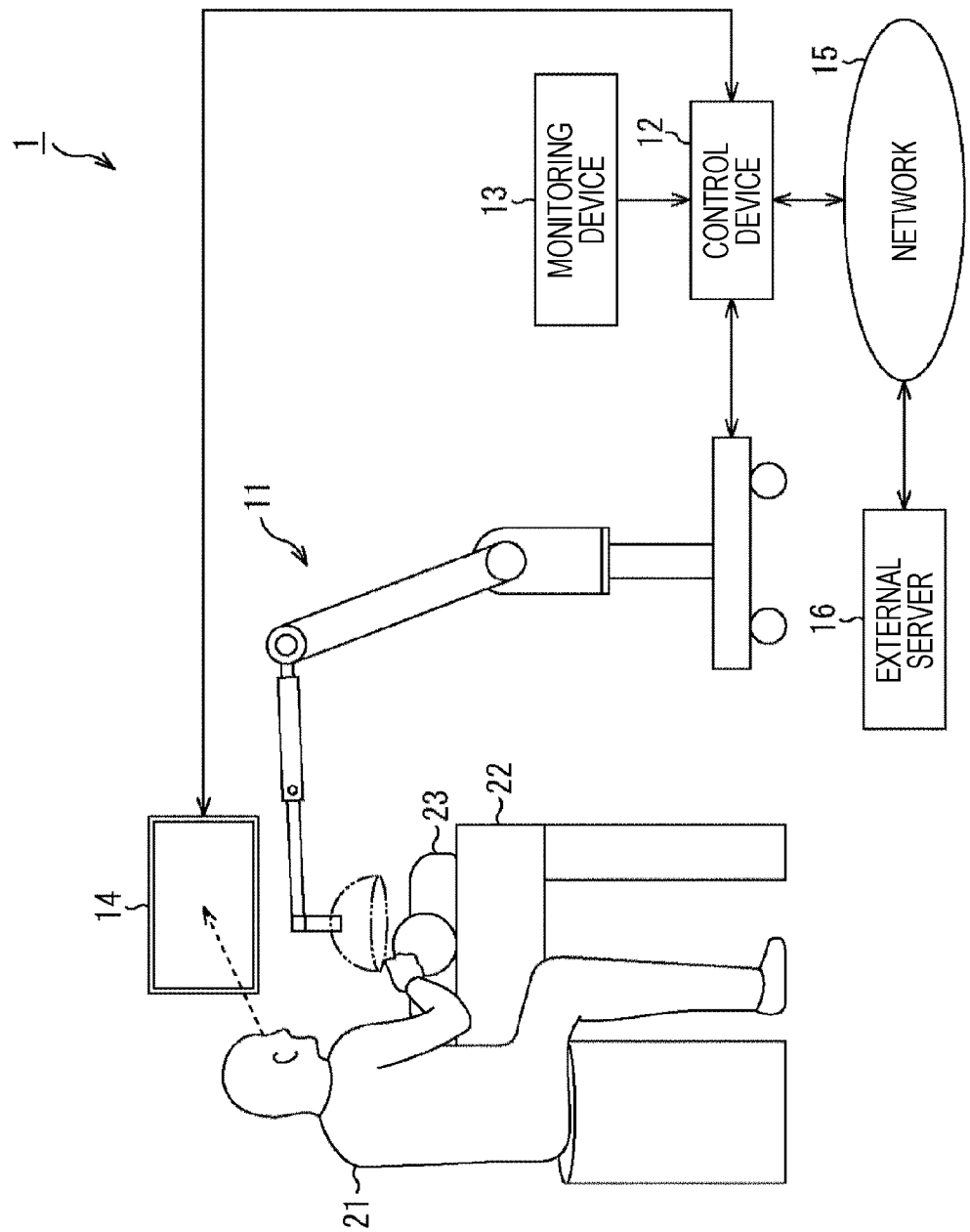
FIG. 1 is a diagram illustrating a state of an operation using a medical display system according to one embodiment of the present technology.

First, an outline of a system to which the present technology may be applied will be described. FIG. 1 is a diagram illustrating a state of an operation using a medical display system according to one embodiment of the present technology.

A medical display system 1 in FIG. 1 includes a microscope device 11, a control device 12, a monitoring device 13, and a display device 14.

In the example in FIG. 1, a state is illustrated in which an operator 21 is performing an operation on a patient 23 on a patient bed 22 using the medical display system 1 including such devices. Note that, in the following description, a "user" means an optional medical staff using the medical display system 1 such as an operator or an assistant.

The microscope device 11 is an electronic imaging microscope device (so-called video-type microscope device). The microscope device 11 images an operative portion of a patient and outputs a signal indicating an operative field image in which an operative field is imaged to the control device 12. Note that, as a device that images the operative field image, a medical imaging device such as an endoscope may be used, instead of the microscope device 11.

The control device 12 is a server device, a personal computer, or the like. The control device 12 generates a display image on the basis of the signal (operative field image signal) of the operative field image supplied from the microscope device 11 and a signal (presented information signal) of presented information supplied from a device including an external device.

Here, the monitoring device 13 is included in the external device. Therefore, a signal (monitoring information signal) of monitoring information supplied from the monitoring device 13 is included in the presented information signal. A signal indicating monitoring information obtained by monitoring biological information (biological reaction) of the patient 23 is supplied from the monitoring device 13.

The control device 12 makes the display device 14 display a display image including the operative field image and the presented information.

Note that communication between the control device 12 with each of other devices may be wired communication or wireless communication.

The control device 12 is connected to an external server 16 via a predetermined network 15, for example, the Internet, a local area network (LAN), or the like. It is also possible to superimpose medical information acquired from the external server 16 on the display image and display the superimposed image on the display device 14.

The monitoring device 13 monitors the biological information of the patient 23 and generates monitoring information indicating a monitoring result of the biological information. The biological information of the patient 23 includes an electrocardiogram, a heart rate, a blood oxygen saturation level, an arterial blood pressure, or the like. The monitoring device 13 outputs a signal indicating the monitoring information to the control device 12.

The display device 14 is provided in the vicinity of the user, such as a wall surface of an operating room. The display device 14 displays the display image generated by the control device 12 according to the control by the control device 12.

The display device 14 displays various types of information regarding an operation such as the biological information and physical information of the patient 23, information regarding an operative procedure of an operation, or the like, together with the operative field image imaged by the microscope device 11. The display on the display device 14 is appropriately switched through an operation by the user. Note that, as the display device 14, various display devices such as a liquid crystal display device or an electro luminescence (EL) display device are used.

In the vicinity of the display device 14, a camera that images a state of a user who performs an operation, a microphone that detects voice of the user, various sensors, or the like are provided. As described later, a user's line-of-sight is detected on the basis of the captured image, and the display on the display device 14 is switched. Furthermore, on the basis of the voice of the user detected by the microphone, the display on the display device 14 is switched, or an operation using the display on the display device 14 is performed.

The external server 16 is, for example, a server device installed in a hospital. The external server 16 stores medical information or the like.

In this way, at the time of the operation using the medical display system 1, the display image generated by the control device 12 is displayed on the display device 14. The user performs various types of treatments such as resection of an affected part while observing the state of the operative portion by viewing the display image displayed on the display device 14.

Figure 2:
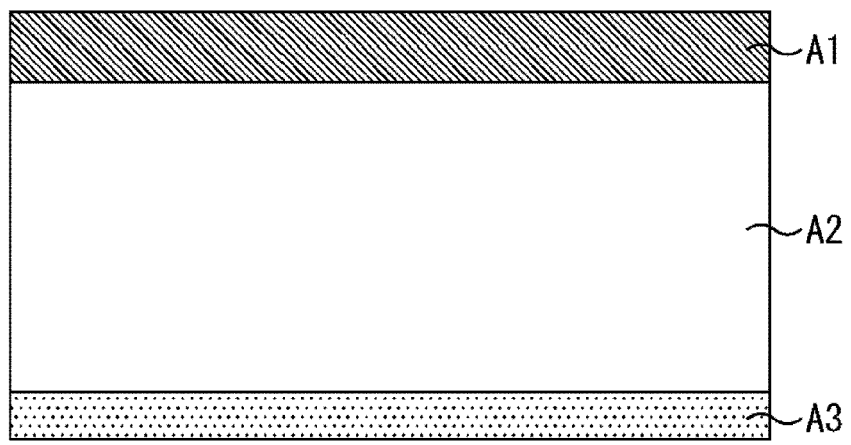
FIG. 2 is a diagram illustrating an example of a region configuration of a display image displayed on a display device.

FIG. 2 is a diagram illustrating an example of a region configuration of the display image displayed on the display device 14.

As illustrated in FIG. 2, the display image is configured by arranging a presented information region A1 and an operation menu region A3 that are narrow belt-like regions on the upper side and lower side of an operative field image region A2 that is a region where an operative field image is displayed.

In the example in FIG. 2, lengths of the presented information region A1, the operative field image region A2, and the operation menu region A3 in the horizontal direction are equal to each other. The operative field image region A2 is a region having a wider width (height) in the vertical direction than the presented information region A1 and the operation menu region A3.

The presented information region A1 is a display region of presented information including the monitoring information indicating the monitoring result by the monitoring device 13 or the like. The presented information region A1 is displayed in a predetermined display form in which the present information includes a text, a graph, or the like.

Figure 3:
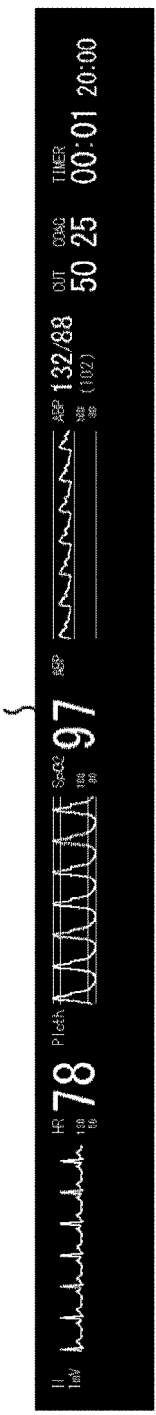
FIG. 3 is an enlarged view illustrating a presented information region in which monitoring information or the like is displayed.

FIG. 3 is an enlarged view illustrating the presented information region A1 in which the presented information including the monitoring information or the like is displayed.

In the example in FIG. 3, from the left side, an electrocardiogram waveform, a heart rate, a pulse wave, a blood oxygen saturation level, and an arterial blood pressure are displayed as the monitoring information. On the right side of the monitoring information, information regarding surgical instruments such as information indicating an output of an electrocautery used by a user and information regarding a time such as a timer are displayed.

In this way, the presented information is information generated from the presented information signal that is acquired from a device including the external device (monitoring device 13 or the like) other than the medical imaging devices such as the microscope device 11. Therefore, in addition to the monitoring information, various types of information needed to be presented to a user, such as the information regarding the surgical instruments and time, is displayed in the presented information region A1 as the presented information.

That is, the presented information can include at least the monitoring information. Therefore, it can be said that the presented information is modality information including the monitoring information. Furthermore, the presented information may include the information regarding the surgical instruments and the time. Moreover, the monitoring information and the information regarding the surgical instruments and the time can be information that changes in real time.

Returning to the description of FIG. 2, the operative field image region A2 that is formed in a wide range at the center of the display image is a display region of the operative field image imaged by the microscope device 11. The operative field image displayed in the operative field image region A2 is an image that changes in real time.

The operation menu region A3 is a display region of an operation menu (operation panel) including various items to be options. By using the display of the operation menu region A3, the user can perform various operations such as selecting an image to be displayed on the display device 14, making the control device 12 communicate with the external server 16, or the like. In this way, in the operation menu region A3, user interface information used for the user's operation is displayed.

Figure 4:
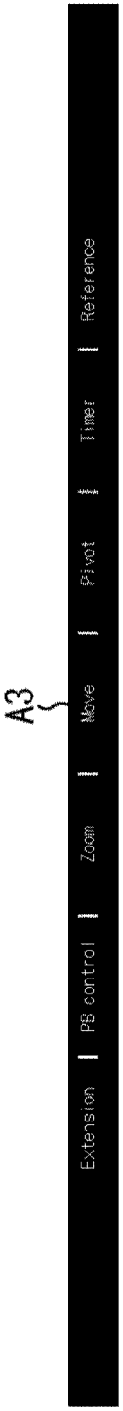
FIG. 4 is an enlarged view illustrating an operation menu region in which an operation menu is displayed.

FIG. 4 is an enlarged view illustrating the operation menu region A3 in which the operation menu is displayed.

In the example in FIG. 4, texts of "Extension", "PB control", "Zoom", "Move", Pivot", "Timer", and "Reference" that represent option items that can be selected by the user are displayed. The user can operate each device such as the control device 12 by selecting the option item. Note that each option item may be displayed as an icon.

"Extension" is an item that is used to make the control device 12 communicate with the external server 16. For example, the user can make a voice call with a user outside the operating room by selecting the item of "Extension".

"PB control" is an item used to make the display device 14 display an operative field image immediately after start of bleeding in a predetermined region in the display image.

"Zoom" is an item that is used to control a display magnification of the operative field image.

"Move" is an item that makes the display device 14 display information used to control a display range of the operative field image.

"Pivot" is an item that is used to control an imaging angle of the microscope device 11 with respect to an operative portion.

"Timer" is an item that is used to make the display device 14 display a timer in the presented information region A1. For example, the user can display an elapsed time together with a preset time in the presented information region A1.

"Reference" is an item that makes the control device 12 execute reference information presentation processing to be described later.

The operation menu including the plurality of option items described above is displayed in the operation menu region A3.

Figure 5A:
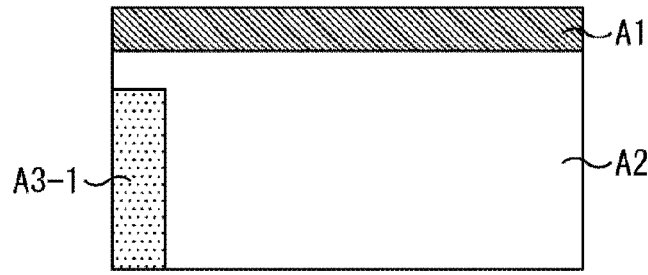
FIGS. 5A, 5B and 5C are diagrams illustrating other examples of the region configurations of the display image.
Figure 5B:
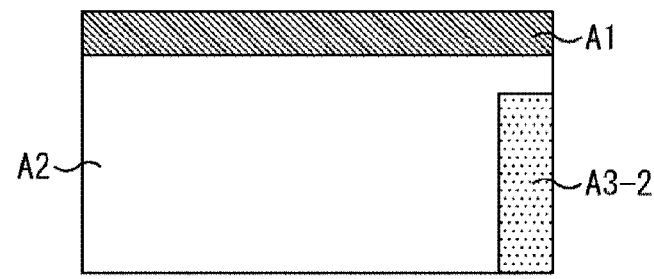

FIGS. 5A, 5B and, 5C are diagrams illustrating another example of the region configuration of the display image.

Figure 5C:
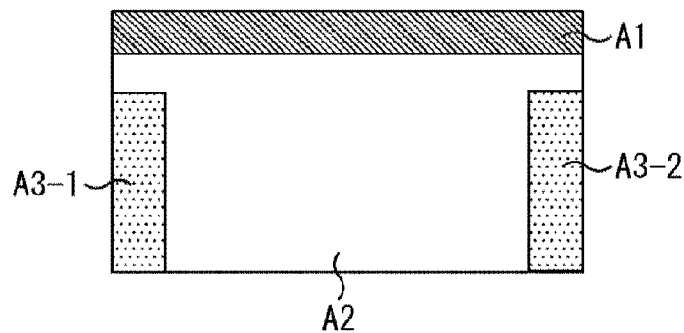

FIGS. 5A, 5B and 5C, display images of which arrangement positions of the operation menu are different from each other are illustrated. Each display image in FIGS. 5A, 5B and, 5C are similar to the display image described with reference to FIG. 2 except that the arrangement positions of the operation menu are different from each other. The overlapped description will be appropriately omitted.

In the example in FIG. 5A, an operation menu region A3-1 that is a display region of an operation menu is arranged at the left end of the display image as a vertically-long region. A predetermined gap is formed between the presented information region A1 and the operation menu region A3-1. In the operation menu region A3-1, for example, the option items are displayed and arranged in the vertical direction. In this case, it is possible to ensure a wider width of the operative field image region A2 in the vertical direction.

In the example in FIG. 5B, an operation menu region A3-2 that is a display region of an operation menu is arranged at the right end to be symmetrical with respect to the operation menu region A3-1 in the display image in FIG. 5A.

In the example in FIG. 5C, the operation menu region A3-1 is arranged at the left end of the display image, and the operation menu region A3-2 is arranged at the right end. In this way, the operation menus may be displayed in two regions at the left end and the right end.

In the example in FIG. 2, a case is illustrated in which it is assumed that a length of the operation menu region A3 in the horizontal direction be equivalent to lengths of the presented information region A1 (upper region) and the operative field image region A2 (middle region) in the horizontal direction and the user interface information is arranged in a lower region that is a region on the lower side thereof. On the other hand, as illustrated in the example in FIGS. 5A, 5B and 5C, it is possible that the length of the operation menu region A3 in the horizontal direction is a different length from the lengths of the presented information region A1 (upper region) and the operative field image region A2 (middle region) in the horizontal direction and the user interface information is arranged in the left and right portion region corresponding to at least one of the regions at the left end or the right end of the middle region. Note that the upper region is, for example, a region including an upper side in a case of a rectangular image. Furthermore, the middle region is a region that includes a right side and a left side and is different from the upper region. Furthermore, the lower region is a region including a lower side.

Figure 6:
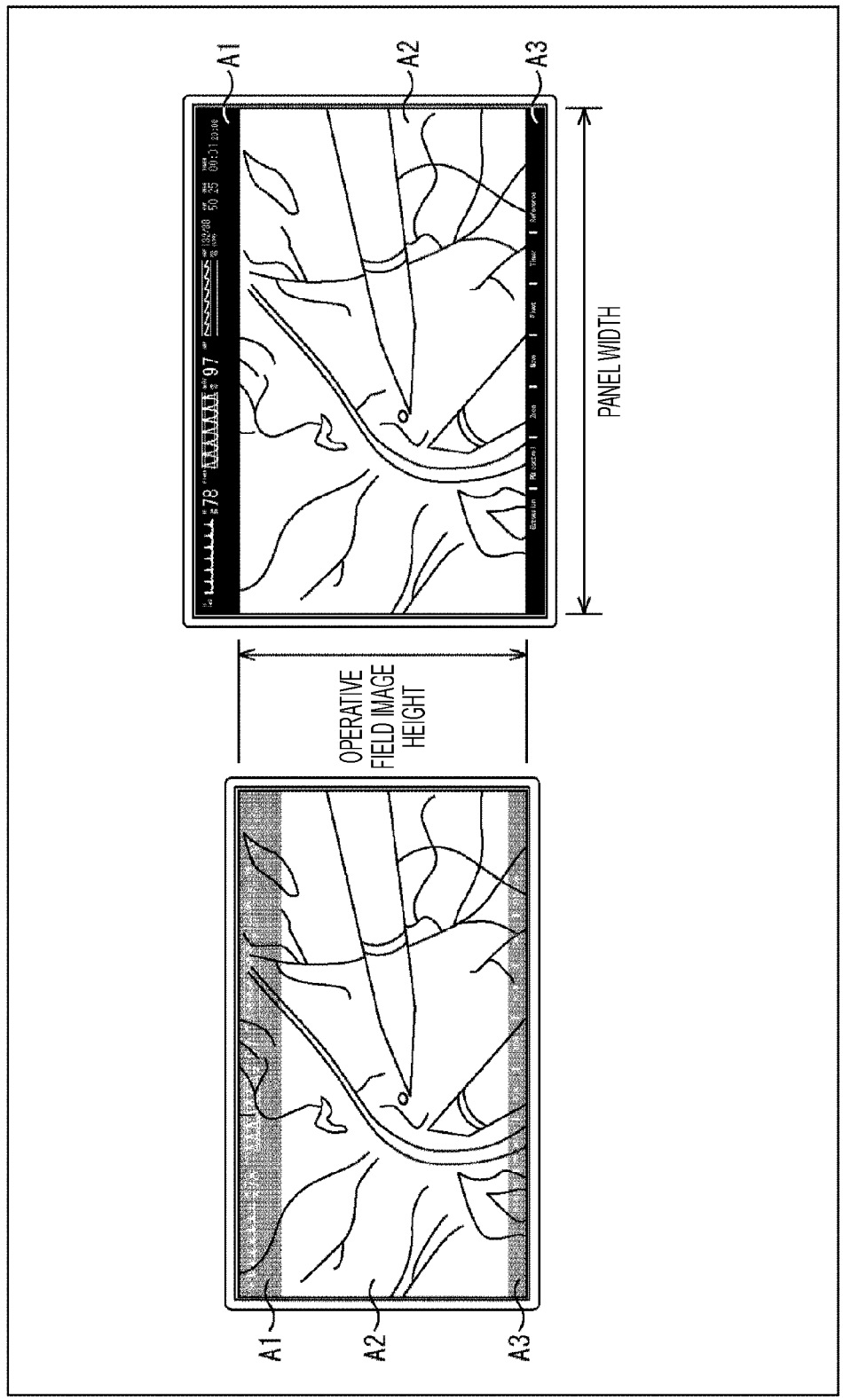
FIG. 6 is a diagram illustrating still other examples of the region configuration of the display image.

FIG. 6 is a diagram illustrating still another example of the region configuration of the display image.

As illustrated in the left side of FIG. 6, the presented information region A1 and the operation menu region A3 may be arranged to be superimposed on the operative field image region A2. At this time, a predetermined transmittance is set to the display in the presented information region A1 and the display in the operation menu region A3. When the presented information in the presented information region A1 and the operation menu in the operation menu region A3 are set as upper layers, a part of the operative field image in the operative field image region A2 is transmitted and viewed as a lower layer.

Note that the region configuration on the right side of FIG. 6 is the same as the region configuration of the display image described with reference to FIG. 2. That is, the presented information region A1 is arranged in contact with the upper portion of the operative field image region A2. The operation menu region A3 is arranged in contact with the lower portion of the operative field image region A2.

As described above, according to the control device 12, it is possible to display the presented information together with the operative field image in a single image in a form of being arranged on the operative field image.

Here, a case is assumed where an operator who is performing an operation often looks at his/her hands even though the operator is performing the operation while viewing the display image displayed on the display device and looks at a person next to (assistant or the like) and other devices. That is, the line-of-sight of the operator tends to be directed rightward, leftward, and downward. On the other hand, there is a high possibility that the operator intentionally looks upward when the line-of-sight of the operator is directed upward.

Furthermore, a paper or the like discloses that asymmetry of visual attention exists in upper and lower hemi-visual fields of humans. That is, it has been known that humans pay more attention to the downward direction than the upward direction.

Here, by displaying the presented information on the upper side of the operative field image, the operator needs to consciously turn the line-of-sight to the presented information in order to view the presented information. Therefore, it is possible to present the presented information without disturbing the concentration of the operator who is performing the operation while viewing the operative field image.

Configuration of Control Device

Figure 7:
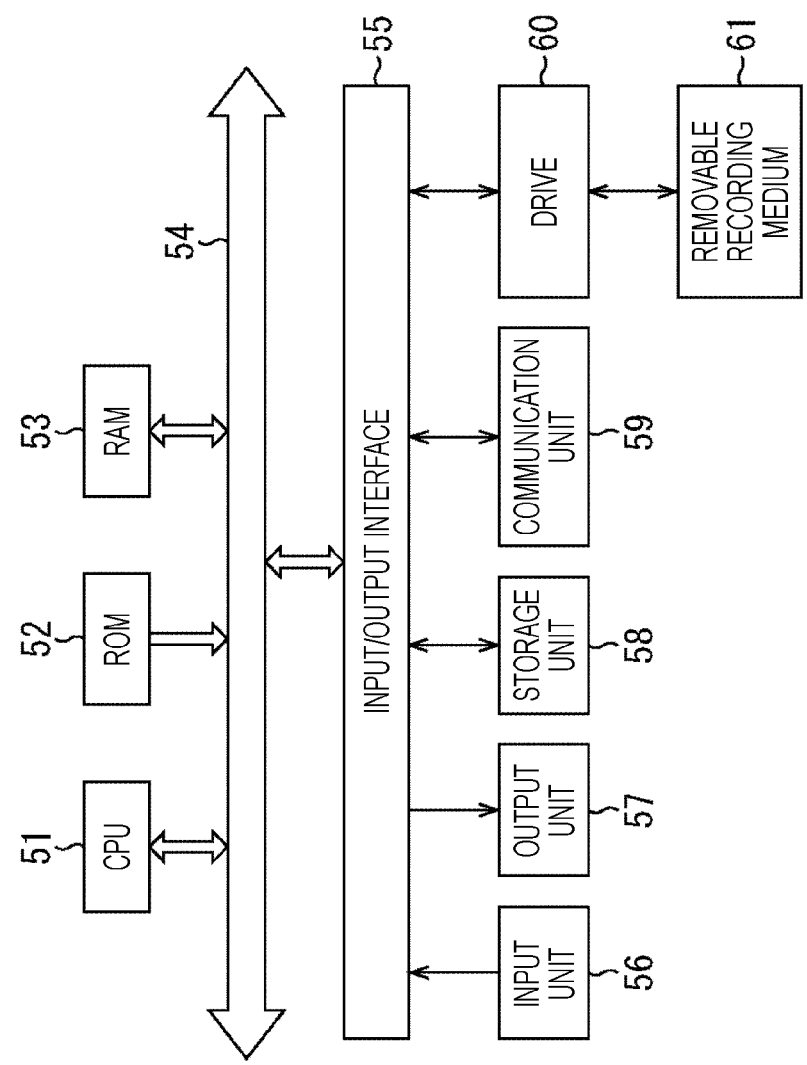
FIG. 7 is a block diagram illustrating a hardware configuration example of a control device.

FIG. 7 is a block diagram illustrating a hardware configuration example of the control device 12.

In the control device 12, a central processing unit (CPU) 51, a read only memory (ROM) 52, a random access memory (RAM) 53 are mutually connected by a bus 54. An input/output interface 55 is further connected to the bus 54. The input/output interface 55 is connected to an input unit 56, an output unit 57, a recording unit 58, a communication unit 59, and a drive 60.

The input unit 56 includes a microphone, a keyboard, a mouse, or the like. The output unit 57 includes a speaker, a display, or the like. The recording unit 58 includes a hard disk, a nonvolatile memory, or the like.

The communication unit 59 includes a network interface or the like. The communication unit 59 communicates with external devices such as the microscope device 11, the monitoring device 13, and the external server 16 connected via the network 15.

The drive 60 drives a removable recording medium 61 such as a magnetic disk, an optical disk, a magnetic optical disk, or a semiconductor memory.

In a computer configured as described above, the CPU 51 loads the programs recorded in the ROM 52 and the recording unit 58 on the RAM 53 via the input/output interface 55 and the bus 54 and executes the programs so as to display the following screen.

Figure 8:
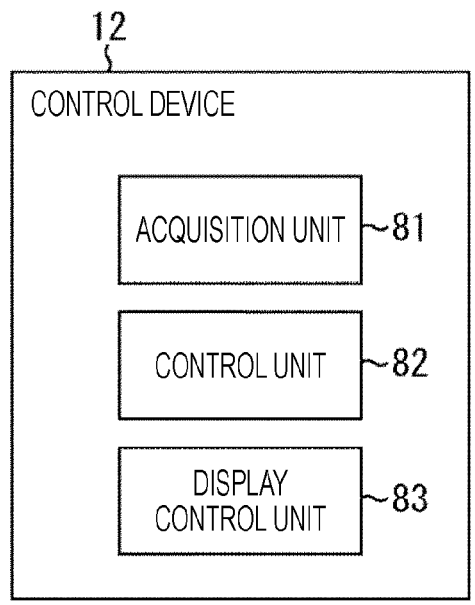
FIG. 8 is a block diagram illustrating a functional configuration example of the control device.

FIG. 8 is a block diagram illustrating a functional configuration example of the control device 12. At least some of the functional units illustrated in FIG. 8 are realized by executing a predetermined program by the CPU 51 in FIG. 7.

As illustrated in FIG. 8, in the control device 12, an acquisition unit 81, a control unit 82, and a display control unit 83 are implemented.

The acquisition unit 81 acquires the signal of the operative field image output from the microscope device 11 and the signal of the presented information output from the external device including the monitoring device 13 by controlling the communication unit 59 in FIG. 7. The signal acquired by the acquisition unit 81 is supplied to the control unit 82. Note that the signal of the presented information may be generated in the control device 12 and may be acquired by the acquisition unit 81.

The control unit 82 generates the presented information and the operative field image on the basis of the signal supplied from the acquisition unit 81. The control unit 82 arranges the presented information in the upper portion of the operative field image and arranges the operation menu in the lower portion of the operative field image so as to generate the display image having the region configuration in FIG. 2. The control unit 82 outputs the display image to the display control unit 83.

The display control unit 83 outputs the display image supplied from the control unit 82 to the display device 14 and makes the display device 14 display the display image.

Behavior of Control Device

Figure 9:
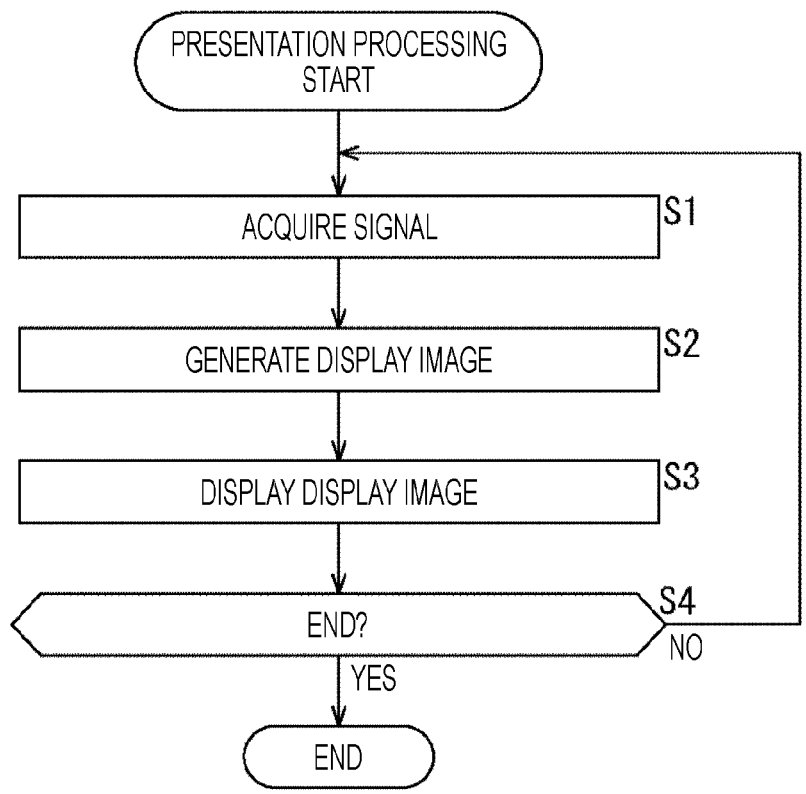
FIG. 9 is a flowchart for explaining presentation processing of the control device.

Next, presentation processing of the control device 12 will be described with reference to the flowchart in FIG. 9.

In step S1, the acquisition unit 81 acquires the signal of the operative field image output from the microscope device 11 and the signal of the presented information output from the external device or the signal of the presented information generated by the control device 12 and outputs the signals to the control unit 82.

In step S2, the control unit 82 generates a display image on the basis of the signal supplied from the acquisition unit 81 and outputs the display image to the display control unit 83.

In step S3, the display control unit 83 outputs the display image to the display device 14 and makes the display device 14 display the display image.

In step S4, the control unit 82 determines whether or not to end the processing.

In a case where it is determined in step S4 not to end the processing, the procedure returns to step S1, and subsequent processing is executed. That is, the operative field image and the presented information that change in real time are updated and are reflected to the display image.

On the other hand, in a case where it is determined in step S4 to end the processing, the presentation processing ends.

According to the above processing, the control device 12 can present the presented information including the monitoring information without disturbing concentration of a user who is performing an operation while viewing the operative field image.

2. Second Embodiment

In this example, a line-of-sight of a user with respect to a display device 14 is detected. A point of regard that is a position on a display image viewed by the user is obtained from the detected line-of-sight, and a method for displaying the presented information region A1 in FIG. 2 is switched on the basis of the obtained point of regard.

Figure 10:
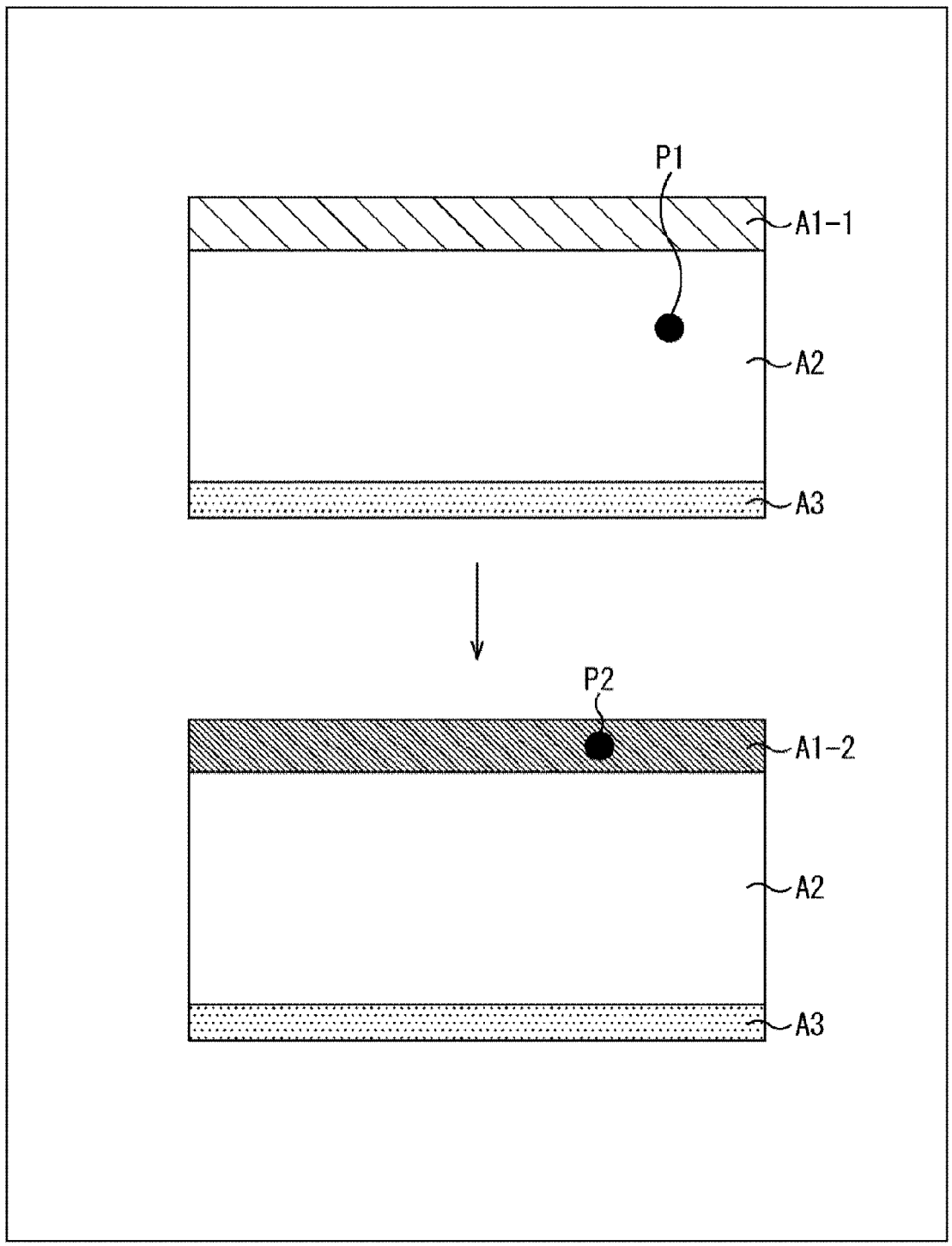
FIG. 10 is a diagram illustrating an example of a method for displaying the presented information region.

FIG. 10 is a diagram illustrating an example of the method for displaying the presented information region A1.

In the upper part of FIG. 10, a presented information region A1-1 that is a display region of presented information and an operation menu region A3 are arranged to be superimposed on an operative field image region A2.

After the display image is displayed on the display device 14, a control device 12 obtains the user's point of regard on the display image. In the example in the upper part of FIG. 10, a point of regard P1 on the display image is obtained on the basis of a user's line-of-sight. In a case where the presented information region A1-1 does not include a point of regard, the control device 12 sets a predetermined transmittance to the display of the presented information region A1-1.

In the example in the lower part of FIG. 10, a point of regard P2 in a presented information region A1-2 is obtained. In a case where the presented information region A1-2 includes a point of regard, the control device 12 generates a display image without setting the transmittance to the display of the presented information region A1-2.

The user's line-of-sight with respect to the display device 14 is detected in real time. The control device 12 controls the transmittance of the presented information region A1 and generates the display image on the basis of the detected line-of-sight.

Figure 11:
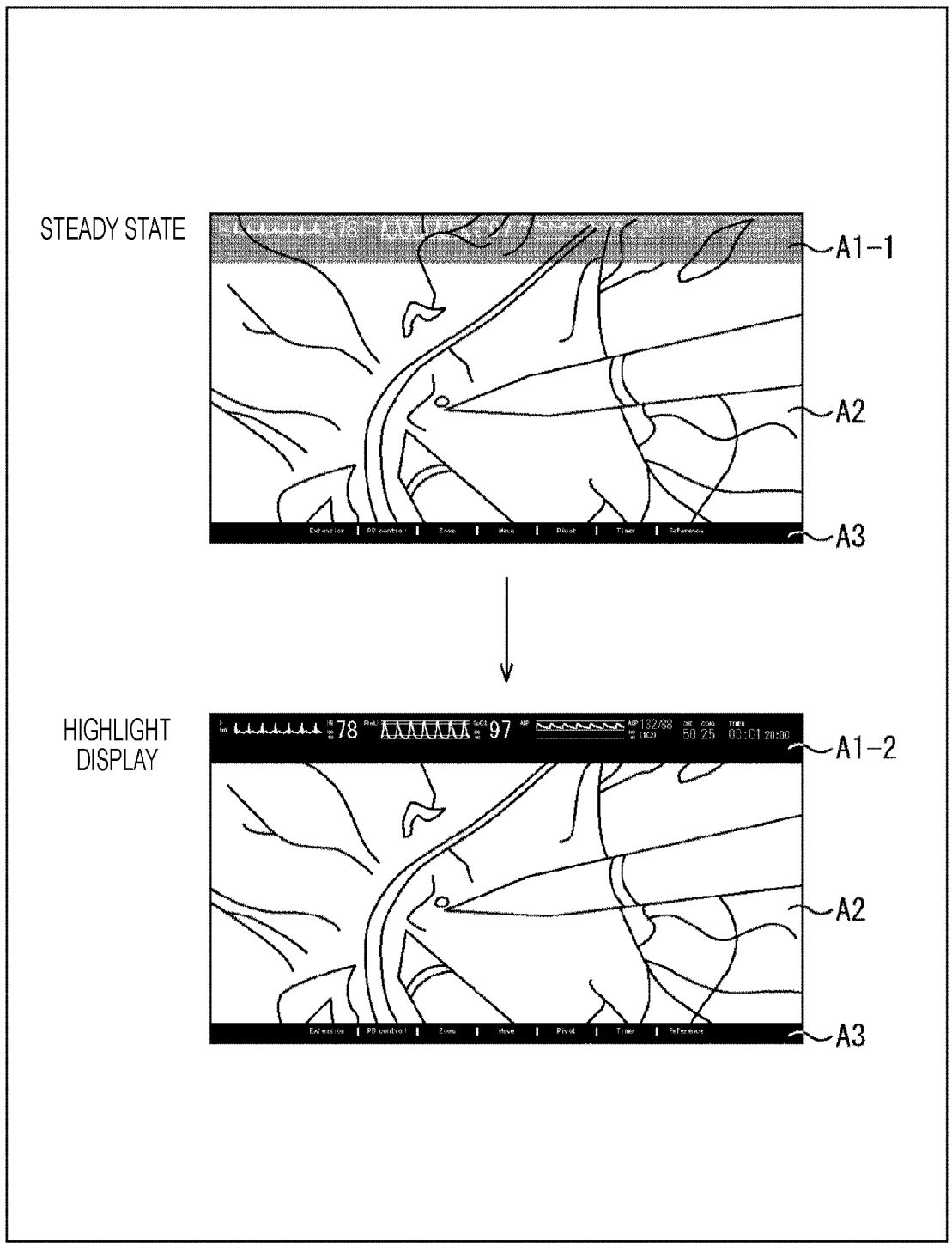
FIG. 11 is a diagram illustrating an example of a method for displaying the presented information region in which presented information is displayed.

Specifically, FIG. 11 illustrates an example of the method for displaying the presented information region A1 in which the presented information is displayed.

The upper part of FIG. 11 illustrates an example of a steady state that is display in a case where the presented information region A1-1 does not include a point of regard. The presented information such as monitoring information similar to that in the presented information region A1 described with reference to FIG. 3 is displayed in the presented information region A1-1 with a predetermined transmittance.

Because the display of the presented information region A1-1 fits into outside of the field of view by displaying the presented information in this steady state, the user can concentrate on manipulation without minding the presented information.

Furthermore, the lower part of FIG. 11 pointed by an arrow illustrates an example of highlight display that is display in a case where the presented information region A1-2 includes a point of regard. The presented information such as the monitoring information similar to that in the presented information region A1 described with reference to FIG. 3 is displayed without setting the transmittance to the presented information region A1-2.

Only in a case where the user needs to view the presented information, the user can clearly view the highlighted presented information by directing the line-of-sight to the presented information region A1-2.

Note that, here, switching between the steady state and the highlight display may be performed on the basis of information regarding the user such as voice, a touch operation, a gesture (behavior), or the like by the user, in addition to the user's line-of-sight.

Furthermore, an example in a case has been described where the switching between the steady state and the highlight display is performed by setting the transmittance. However, the steady state and the highlight display may be switched by another setting on the display of the presented information region A1. For example, the steady state and the highlight display may be switched through a change in a luminance, a change in a display color, or an inversion of the display color of the display of the presented information region A1.

Figure 12:
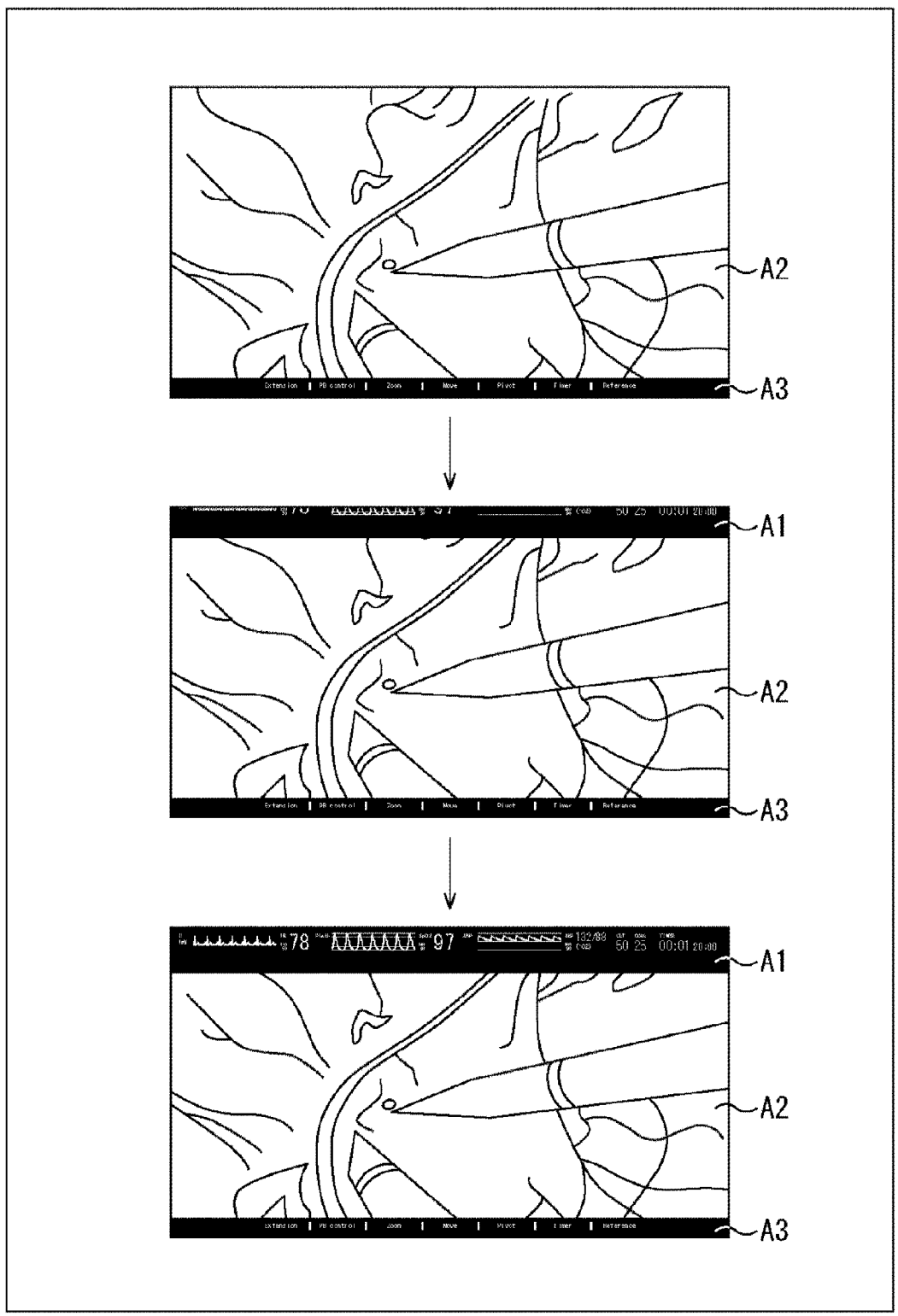
FIG. 12 is a diagram illustrating another example of the method for displaying the presented information region in which the presented information is displayed.

FIG. 12 is a diagram illustrating another example of the method for displaying the presented information region A1 in which the presented information is displayed.

In a case where the user's line-of-sight is not directed to the presented information region A1, in the example in the upper part of FIG. 12, a display image including the operative field image region A2 and the operation menu region A3 that are regions other than the presented information region A1 is displayed.

In a case where the user's line-of-sight is directed to a predetermined region, in the examples in the middle part and the lower part of FIG. 12, the presented information region A1 is gradually displayed from the lower part to the upper part as time elapses. For example, in a case where the user's line-of-sight is detected on an upper side of the operative field image region A2, the presented information is displayed. Furthermore, in a case where the user's line-of-sight is directed to the predetermined region, the presented information may be displayed in a fade-in manner.

Next, highlight display processing of the control device 12 will be described with reference to the flowchart in FIG. 13.

Figure 13:
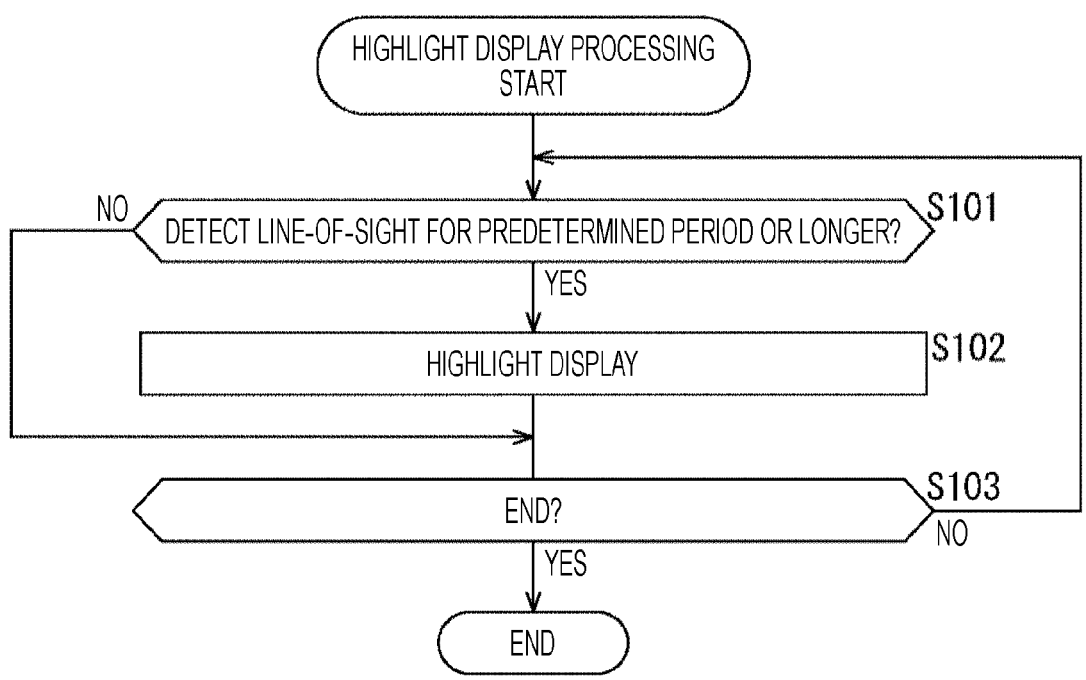
FIG. 13 is a flowchart for explaining highlight display processing of the control device.

The highlight display processing in FIG. 13 starts after the display image in the steady state is displayed on the display device 14.

In step S101, the control unit 82 detects a user's line-of-sight on the basis of a captured image imaged by a camera. The control unit 82 obtains a point of regard on the display image on the basis of the detected user's line-of-sight and determines whether or not the line-of-sight with respect to the presented information region A1 for a predetermined period or longer is detected on the basis of the obtained point of regard.

In a case where it is determined in step S101 that the line-of-sight with respect to the presented information region A1 for the predetermined period or longer is detected, the procedure proceeds to step S102.

In step S102, the control unit 82 generates a display image by arranging the presented information to be displayed as highlight display and outputs the display image to the display control unit 83. The display control unit 83 outputs the display image supplied from the control unit 82 to the display device 14 and makes the display device 14 display the display image.

In step S103, the control unit 82 determines whether or not to end the highlight display processing. In a case where it is determined in step S101 that the line-of-sight with respect to the presented information region A1 for the predetermined period or longer is not detected, step S102 is skipped, the procedure proceeds to step S103, and it is determined whether or not to end the highlight display processing.

In a case where it is determined in step S103 not to end the highlight display processing, the procedure returns to step S101, and subsequent processing is executed.

On the other hand, in a case where it is determined in step S103 to end the highlight display processing, the highlight display processing ends.

According to the above processing, it is possible to present the presented information without disturbing concentration of a user who is performing an operation while viewing an operative field image. Furthermore, it is possible to clearly present the presented information only when the user needs the presented information.

3. Third Embodiment

In a case where an item of "Reference" in an operation menu is selected, a control device 12 executes reference image presentation processing. Hereinafter, a case where "Reference" is selected will be described.

Figure 14A:
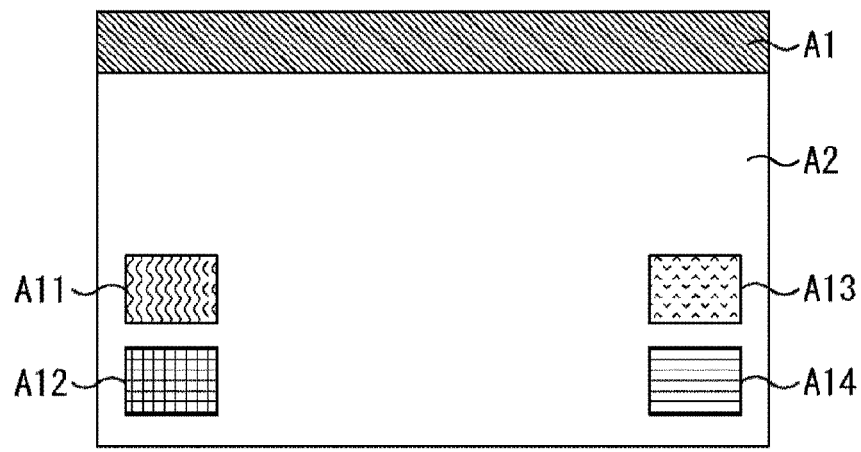
FIGS. 14A and 14B are diagrams illustrating an example of a region configuration of a display image displayed on a display device in a case where "Reference" is selected.
Figure 14B:
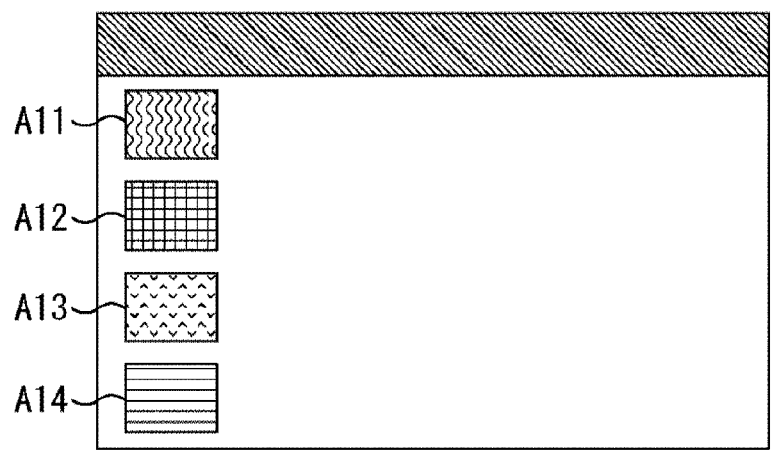

FIGS. 14A and 14B are diagrams illustrating an example of a region configuration of a display image displayed on a display device 14 in a case where "Reference" is selected.

As illustrated in of FIGS. 14A and 14B, the display image in a case where "Reference" is selected is configured by arranging a presented information region A1 that is a narrow belt-like region on an upper side of an operative field image region A2 that is a region where an operative field image is displayed and arranging reference information group regions A11 to A14 that are rectangular regions to be superimposed on the operative field image region A2.

Because each display image in FIGS. 14A and 14B is similar to the display image with reference to FIG. 2 except that that an operation menu region A3 is not included and the reference information group regions A11 to A14 are provided, overlapped description will be appropriately omitted.

In the example in FIG. 14A, the reference information group regions A11 and A12 are arranged side by side in the vertical direction on the left side of the display image. A predetermined gap is formed between the reference information group regions A11 and A12 and the left end of the display image. Furthermore, predetermined gaps are respectively formed between the reference information group region A12 and the lower end of the display image and between the reference information group region A11 and the presented information region A1.

Moreover, in the example in FIG. 14A, the reference information group regions A13 and A14 are arranged on the right side of the display image to be symmetrical with respect to the reference information group regions A11 and A12.

The reference information group regions A11 to A14 are display regions of reference images. The reference image includes monitoring information indicating a monitoring result by a monitoring device 13 and medical information acquired from an external server 16. The medical information includes a pathological image, an ultrasound image, an indocyanine green (ICG) image, a magnetic resonance imaging (MRI) image, a computed tomography (CT) image, an angiographic image (angiographic image), and an X-ray image, or the like.

The reference images are divided into predetermined reference information groups. In the reference information group regions A11 to A14, information indicating the reference information group is displayed for each reference information group.

The positions of the reference information group regions A11 to A14 in the display image may be determined on the basis of a category of the reference information group. At this time, pieces of the information regarding the respective reference information groups in the same category of the reference information group are displayed side by side on the same side that is one of the left side or the right side of the display image. For example, in the reference information group regions A11 and A12, the monitoring information and the reference image such as an ultrasound image that is updated in real time are displayed, and in the reference information group regions A13 and A14, reference images that are prepared before start of an operation such as an MRI image or a CT image are displayed.

As illustrated in FIG. 14B, the reference information group regions A11 to A14 may be arranged in the vertical direction on the left side of the display image. Furthermore, the reference information group regions A11 to A14 may be arranged on the right side of the display image to be symmetrical with respect to the reference information group regions A11 to A14 in the display image in FIG. 14.

Figure 15:
FIG. 15 is a diagram illustrating an example of a display image in which information indicating a reference information group is displayed.

FIG. 15 is a diagram illustrating an example of a display image in which the information regarding the reference information group is displayed.

In the example in FIG. 15, as the information indicating the reference information group, thumbnail images corresponding to the reference information group are displayed in the reference information group regions A11 to A14.

In the example in FIG. 15, the reference images are classified into four groups including the monitoring information, the ultrasound image, the ICG image, and the MRI image as the reference information groups. As thumbnail images corresponding to the reference information groups displayed in the reference information group regions A11 to A14, images indicating the monitoring information, the ultrasound image, the ICG image, and the MRI image are respectively used. Note that an optional group may be set as the reference information group, and an optional image may be used as the thumbnail image. For example, a surgical navigation image indicating a surgical navigation may be set as the reference information group, and the surgical navigation image may be displayed in the reference information group region. Note that, as the thumbnail image, one of the reference images associated with the respective groups may be selected and used as the thumbnail image.

Figure 16A:
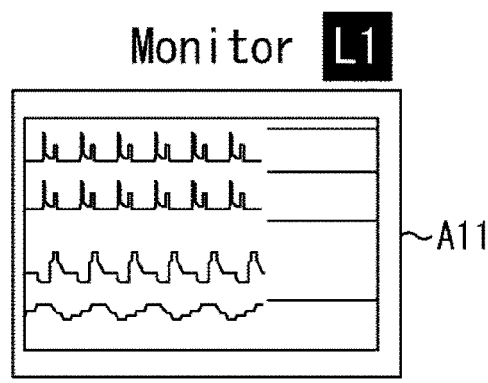
FIGS. 16A and 16B are enlarged view illustrating a main reference information group region in which a thumbnail image is displayed.
Figure 16B:
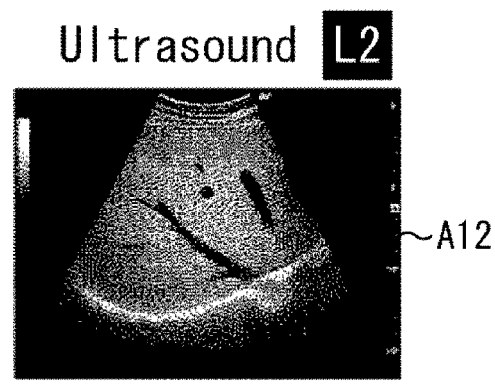

FIGS. 16A and 16B are enlarged view illustrating the reference information group region A11 in which the thumbnail image of the monitoring information is displayed and the reference information group region A12 in which the thumbnail image of the ultrasound image is displayed.

In the example in FIG. 16A, the pieces of monitoring information indicating the monitoring result by the monitoring device 13 are arranged in the vertical direction and displayed in the reference information group region A11 as thumbnail images indicating the monitoring information. The monitoring information displayed in the reference information group region A11 may be information including the monitoring information displayed in the presented information region A1 described with reference to FIG. 3.

In the upper portion of the reference information group region A11, a name of the displayed reference information group and a number or a symbol representing the reference information group are displayed. In the example in FIG. 16B, in the upper portion of the reference information group region A11, a text "Monitor" is displayed as the name of the monitoring information that is the reference information group. Furthermore, on the right side of the text "Monitor", a text "L1" is displayed as a symbol representing the monitoring information.

In the example in FIG. 16B, an ultrasound image acquired from the external server 16 is displayed in the reference information group region A12 as a thumbnail image indicating the ultrasound image.

As in the reference information group region A11, in an upper portion of the reference information group region A12, a text "Ultrasound" is displayed as a name of the ultrasound image that is the reference information group. Furthermore, on the right side of the text "Ultrasound", a text "L2" is displayed as a symbol representing the ultrasound image.

The user can display a list of the reference images included in the selected reference information group by selecting the displayed thumbnail image. At this time, for example, the user can select the thumbnail image of the reference information group with a line-of-sight or voice.

In a case where voice input is performed, the user can select the thumbnail image of the reference information group by uttering the name of the reference information group or the symbol representing the reference information group as voice. Furthermore, in a case where line-of-sight input is performed, the user can reliably select a necessary reference information group by viewing the name of the reference information group.

Figure 17:
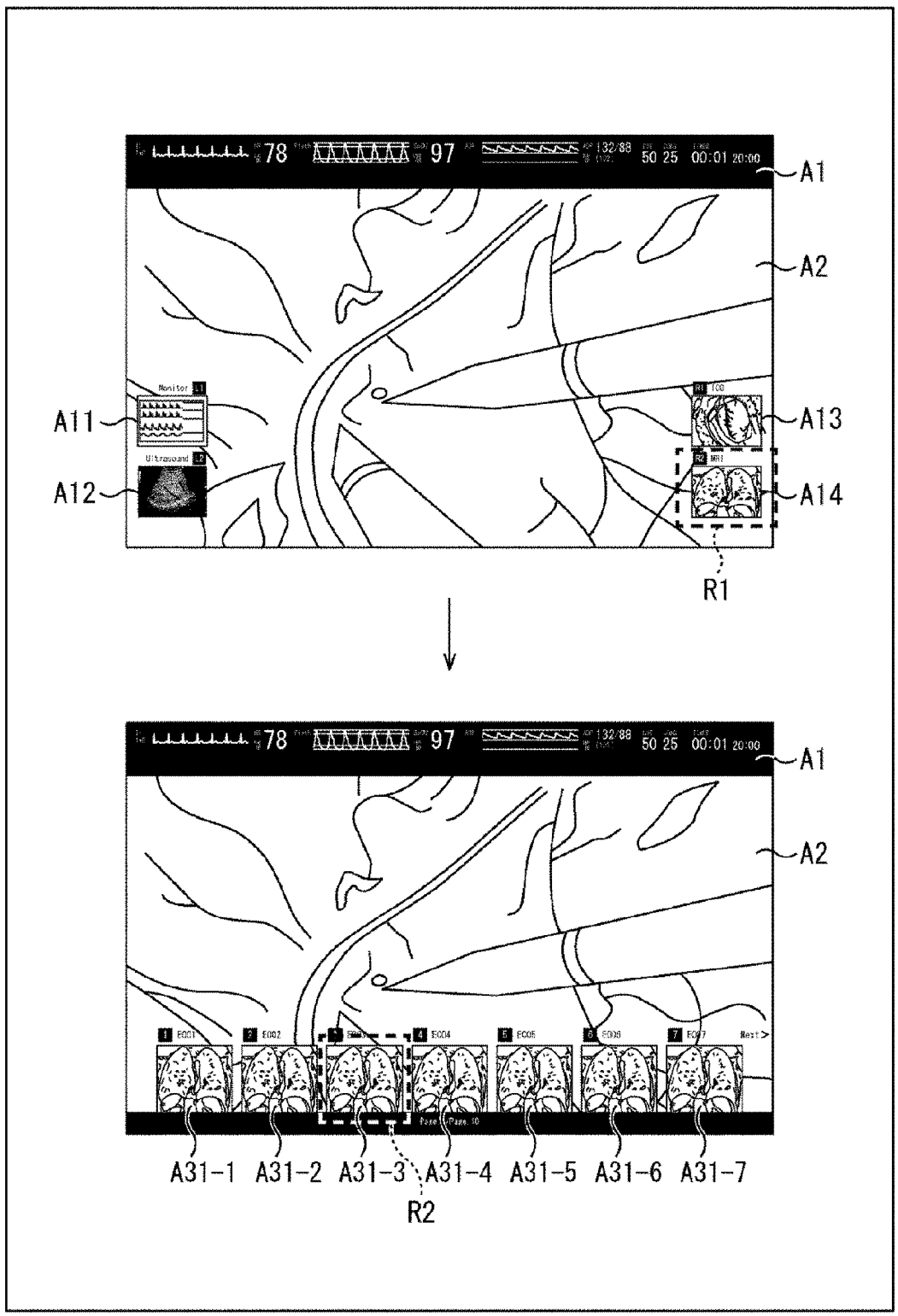
FIG. 17 is a diagram illustrating an example of a display image in which a list of reference images is displayed.

FIG. 17 is a diagram illustrating an example of a display image in which a list of reference images is displayed.

A display image in an upper part of FIG. 17 is a display image same as the display image, in which the thumbnail image of the reference information group is displayed, described with reference to FIG. 15. A dashed rectangle R1 on the obliquely lower right in the display image indicates that a thumbnail image of an MRI image displayed in the reference information group region A14 is selected.

In a case where the MRI image is selected, for example, the control device 12 generates a display image illustrated in a lower part of FIG. 17. In the example of the display image in the lower part of FIG. 17, the presented information region A1 is arranged on the operative field image region A2, and rectangular reference image regions A31-1 to A31-7 are arranged to be superimposed on the operative field image region A2 so as to form the display image.

That is, in the example of the display image in the lower part of FIG. 17, the reference image regions A31-1 to A31-7 are arranged so as to move from the right side to the left side in this order after the images displayed in the reference information group regions A11 to A14 disappear, and the reference image regions A31-1 to A31-7 are arranged in the horizontal direction on the lower side of the display image.

The reference image regions A31-1 to A31-7 are display regions of the reference images included in the reference information group selected by the user. In the example of the display image in the lower part of FIG. 17, reference images that are different MRI images are respectively displayed in the reference image regions A31-1 to A31-7. Note that, in the example in the lower part of FIG. 17, an example in a case where the number of reference image regions is seven is illustrated. However, any number of reference image regions included in the display image may be used.

In a case where the number of reference images included in the reference information group selected by the user is larger than the number of reference image regions included in the display image, the reference images as many as the reference image regions are displayed in the display image. In this case, by receiving a predetermined user's operation, the control device 12 switches the reference image displayed in the reference image region. In the example of the display image in the lower part of FIG. 17, information regarding the number of reference images included in the selected reference information group is displayed in the operation menu. Note that, at this time, operation items such as "Go Back" to return to a selection screen of the reference information group and "Cancel" to cancel the selection of the reference image and stop the display of the reference image may be displayed in the operation menu.

In a case where the number of reference images included in the reference information group selected by the user is one, the display image including the reference image region is not generated, and a display image in which the reference image is displayed in a selection reference image region to be described later is generated.

Furthermore, in upper portions of the reference image regions A31-1 to A31-7 in which the reference images are displayed, the number or symbol representing each of the displayed reference images is displayed.

The user selects a reference image to be displayed so as to display only the selected reference image among the reference images included in the reference information group. At this time, for example, the user can select a reference image with a line-of-sight or voice.

In a case where voice input is performed, the user can select the reference image by uttering the number or the symbol representing each reference image as voice.

A dashed rectangle R2 illustrated in the lower side of the display image in the lower part of FIG. 17 indicates that a reference image displayed in the reference image region A31-3 is selected by the user.

Figure 18:
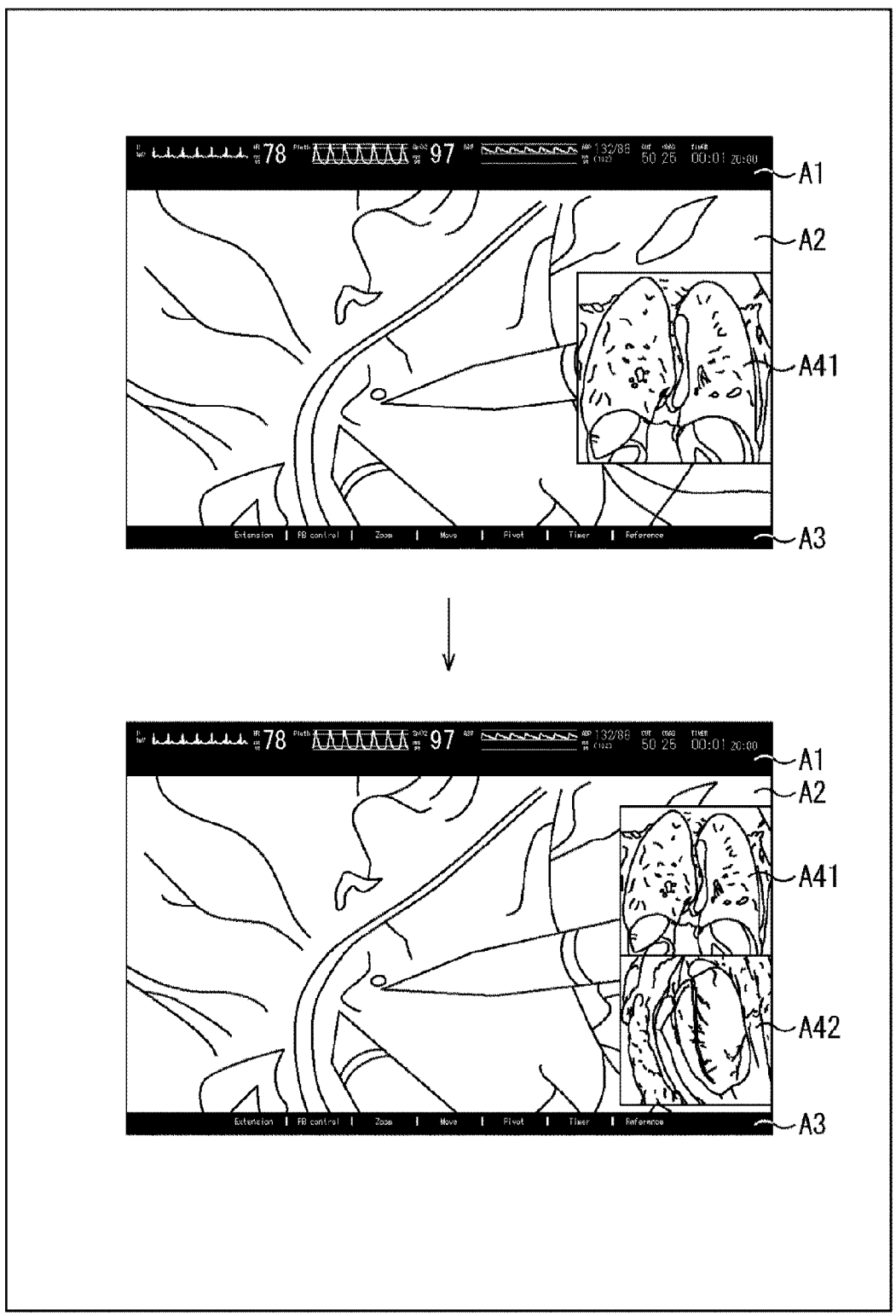
FIG. 18 is a diagram illustrating an example of a display image in which a selected reference image is displayed.

FIG. 18 is a diagram illustrating an example of a display image in which a selected reference image is displayed.

A display image in the upper part of FIG. 18 is a display image that is displayed after the display image displayed in the reference image region A31-3 in FIG. 17 is selected. In the example of the display image in the upper part of FIG. 18, a rectangular selection reference image region A41 is arranged to be superimposed on the display image described with reference to FIG. 2. In the example of the display image in the upper part of FIG. 18, the selection reference image region A41 is arranged at the right end of the display image. Predetermined gaps are respectively formed between the selection reference image region A41 and the presented information region A1 and between the selection reference image region A41 and the operation menu region A3.

The selection reference image region A41 is a display region of the reference image selected by the user from among the list of the reference images included in the reference information group. In the example of the display image in the upper part of FIG. 18, an MRI image selected by the user is displayed in the selection reference image region A41. Note that, in order to easily view a target site or the like, the operative field image region A2 may be arranged to be shifted to a direction opposite to the selection reference image region A41.

When a reference image different from the reference image displayed in the selection reference image region A41 is selected after the reference image is displayed in the selection reference image region A41, as illustrated in the lower part of FIG. 18, regarding the display image, the rectangular selection reference image regions A41 and A42 may be arranged to be superimposed on the display image described with reference FIG. 2.

In the example of the display image in the lower part of FIG. 18, the selection reference image regions A41 and A42 are arranged in the vertical direction and at the right end of the display image. As in the selection reference image region A41, the selection reference image region A42 is a display region of the reference image selected by the user from among the list of the reference images included in the reference information group. In the example of the display image in the lower part of FIG. 18, an ICG image is displayed in the selection reference image region A42. Note that, when the user selects a third reference image in a state where two reference images are displayed, the first reference image is displayed in the display region in which the second reference image is displayed, and then, the third reference image may be displayed in the display region in which the second reference image is displayed. Furthermore, when "Reference" is selected again after the display of the reference image is deleted due to the selection of the item "Cancel" by the user, the control device 12 may display or present a reference image selected at the time of previous selection of "Reference" as a reference image again or to the user as a candidate image. The candidate image is an image to which a visual effect different from that of the other images in the list of the reference images is applied so that the candidate image can be recognized as the reference image that is selected at the previous time.

Figure 19:
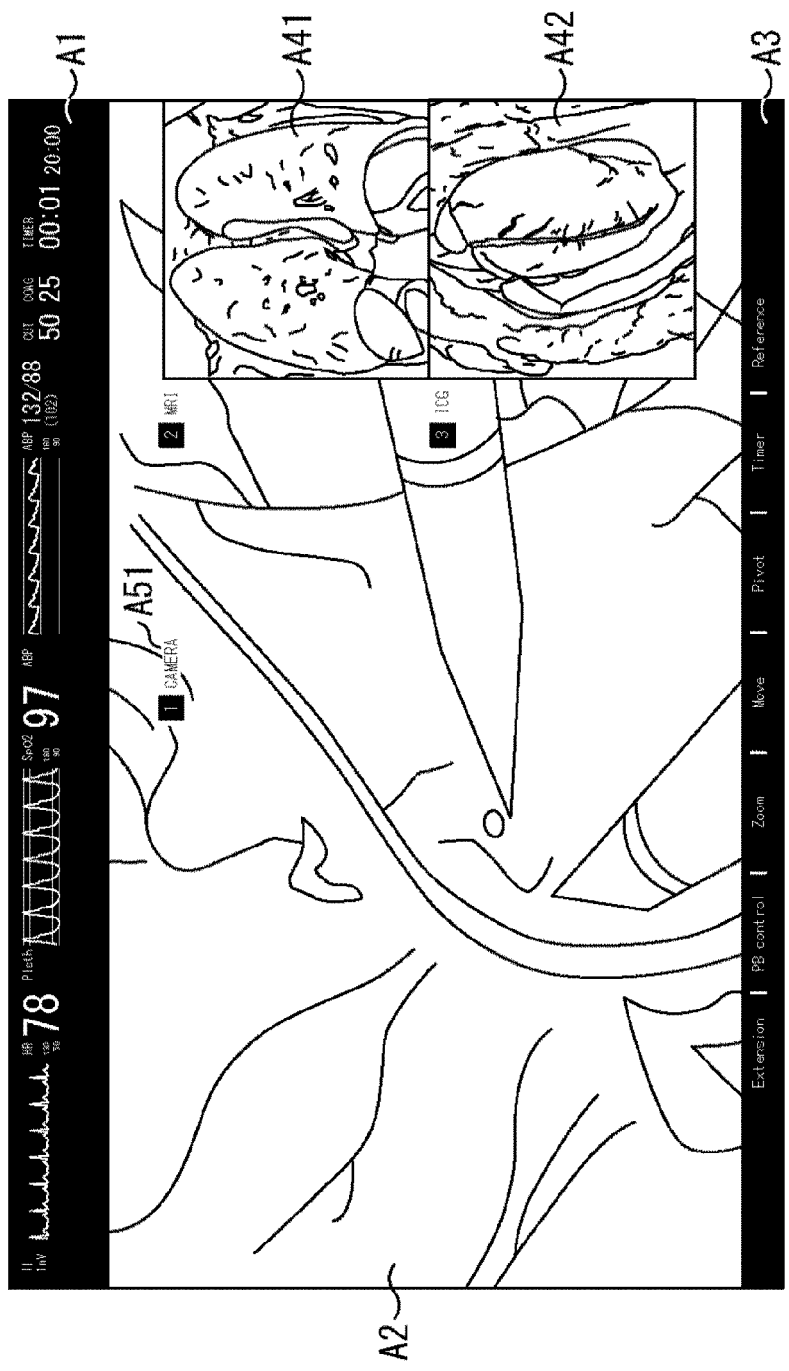
FIG. 19 is an enlarged view of a display image in which two reference images selected by a user are displayed.

FIG. 19 is a diagram illustrating an example in a case where a display image in which two reference images selected by a user are displayed is enlarged.

The display image in FIG. 19 is similar to the display image illustrated in the lower part of FIG. 18 except that the text is displayed to be superimposed on the operative field image. Therefore, overlapped description will be appropriately omitted.

In the example in FIG. 19, the numbers and the names respectively indicating the reference images displayed in the selection reference image regions A41 and A42 are displayed on the left side of the selection reference image regions A41 and A42. The user can select the displayed reference image with a line-of-sight and can enlarge and display the selected reference image on the display image. Furthermore, the displayed reference image may be selected by uttering the number or the name indicating the reference image as voice by the user.

As illustrated in FIG. 19, an operation indicator region A51 may be arranged to be superimposed on the operative field image region A2. In the example in FIG. 19, the operation indicator region A51 is arranged on the upper side of the operative field image region A2. The position in the display image where the operation indicator region A51 is arranged may be determined by the control device 12 on the basis of a user's line-of-sight detected by the control device 12.

The operation indicator region A51 includes a display region having the number or the name indicating the operative field image displayed in the operative field image region A2. In the example in FIG. 19, a text "CAMERA" as the name indicating the operative field image is displayed in the operation indicator region A51 together with the number indicating the operative field image.

The user can select the operative field image by turning the line-of-sight to the operation indicator region A51 and can display an initial state, that is, the display image including the presented information region A1, the operative field image region A2, and the operation menu region A3 described with reference to FIG. 2. Furthermore, the operative field image may be selected by uttering the number or the name indicating the operative field image as voice by the user.

As described above, according to the control device 12, it is possible to display the presented information and the operative field image in a single image in a form in which the presented information is arranged on the operative field image and to display the reference image necessary for the operation among the reference images acquired from the external server 16 outside the operating room.

Note that, in a case where the user selects the item "Reference" is selected from the operation menu, another piece of information different from the thumbnail image of the reference information group may be displayed in the reference information group region as information indicating the reference information group.

Figure 20:
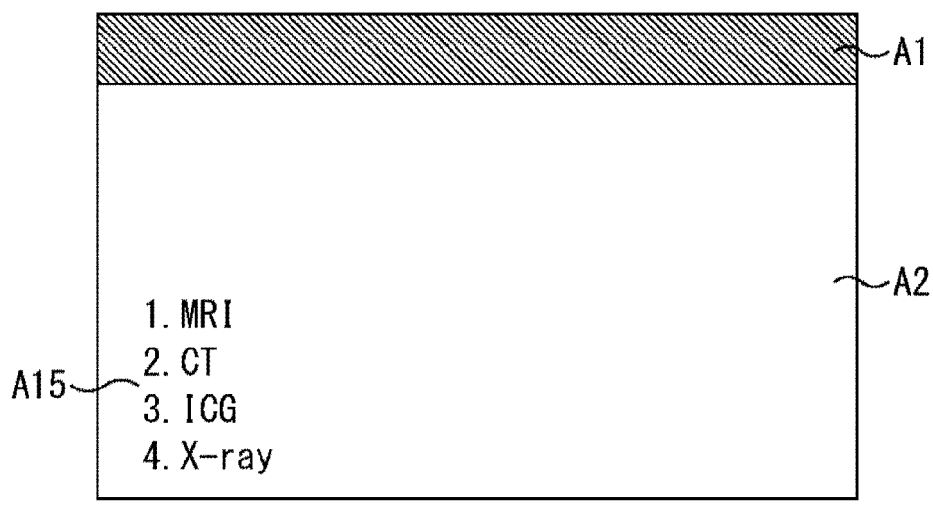
FIG. 20 is a diagram illustrating another example of a region configuration of the display image in which the information indicating the reference information group is displayed.

FIG. 20 is a diagram illustrating an example of another region configuration of the display image in which the information indicating the reference information group is displayed.

In FIGS. 20A and 20B, a region configuration of a display image in which an index is displayed as a text as the information indicating the reference information group is illustrated. Because the display image in FIGS. 20A and 20B are similar to the display image described with reference to FIGS. 14A and 14B except that the number and arrangement of the reference information group regions are different, overlapped description will be appropriately omitted.

In the example in FIG. 20, a reference information group region A15 that is a display region of information indicating a reference information group is arranged at the left end of the display image. Note that the reference information group region A15 may be arranged at the right end of the display image.

In the example in FIG. 20, an index that is the list of the reference information groups is displayed as a text in the reference information group region A15. The index includes, for example, a name of the reference information group and a number indicating the reference information group.

Even in a case where the index is displayed as the information indicating the reference information group, as in a case where a thumbnail image is displayed as the information indicating the reference information group, the user can select the reference information group with a predetermined line-of-sight or voice and display a list of reference images included in the selected reference information group.

Furthermore, an example of a case where the list of the reference images included in the selected reference information group is displayed on the lower side of the display image has been described with reference to FIG. 17. However, a position where the list of the reference images is displayed may be determined by the control device 12 on the basis of a user's line-of-sight or the like.

Figure 21A:
FIGS. 21A and 21B are diagrams illustrating another example of the display image in which the list of the reference images is displayed.
Figure 21B:

FIGS. 21A and 21B are diagrams illustrating another example of the display image in which the list of the reference images is displayed.

In FIGS. 21A and 21B, a display image of which an arrangement position of a reference image is different from that of the display image described with reference to FIG. 17 is illustrated. Because each display image in FIGS. 21A and 21B are similar to the display image described with reference to FIG. 17 except that the arrangement position of the reference image is different, overlapped description will be appropriately omitted.

In the example in FIG. 21A, the reference image regions A31-1 to A31-4 that are the display regions of the reference images included in the reference information group selected by the user are arranged in the vertical direction at the left end of the display image as a rectangular region. Different reference images are displayed in the respective reference image regions A31-1 to A31-4.

In the example in FIG. 21A, an example of a case where the number of reference image regions included in the display image is four has been described. However, any number of reference image regions may be used. In a case where the number of reference images included in the reference information group selected by the user is larger than the number of reference image regions, the reference images as many as the reference image regions are displayed in the display image. In this case, by receiving a predetermined user's operation, the control device 12 switches the reference image displayed in the reference image region so as to generate the display image as illustrated in FIG. 21B.

The display image in FIG. 21B is a display image in which the reference image regions A31-1 to A31-4 of the display image in FIG. 21A are replaced with reference image regions A31-5 to A31-8 that are display regions of reference images included in the reference information group selected by the user. In the reference image regions A31-5 to A31-8, reference images different from the reference images displayed in the reference image regions A31-1 to A31-4 are respectively displayed.

Figure 22A:
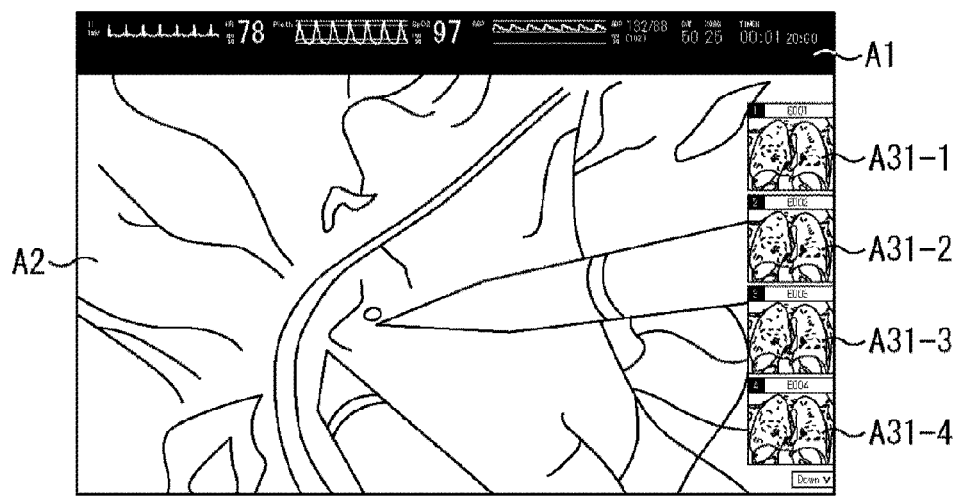
FIGS. 22A and 22B are diagrams illustrating still another example of the display image in which the list of the reference images is displayed.
Figure 22B:
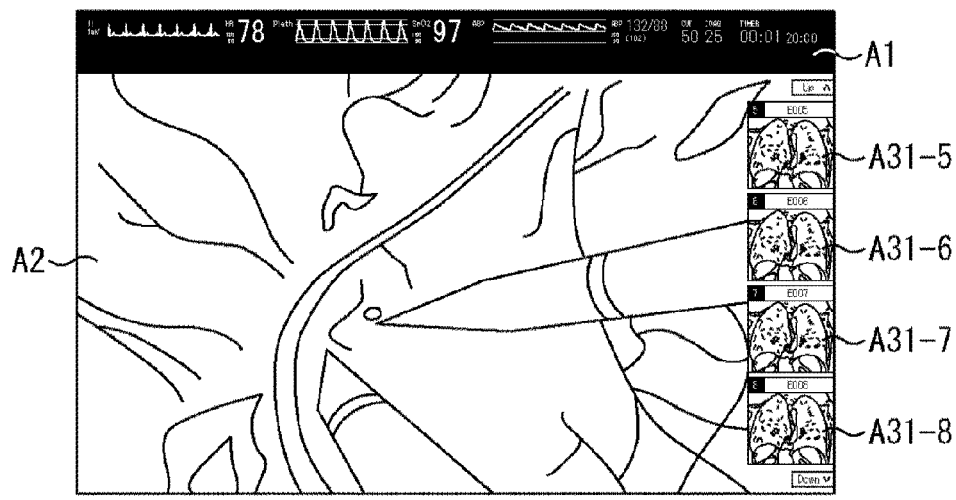

FIGS. 22A and 22B are diagrams illustrating still another example of the display image in which the list of the reference images is displayed.

In the example in FIGS. 22A and 22B, reference image regions A31-1 to A31-8 are arranged at the right end of the display image to be symmetrical with respect to the reference image regions A31-1 to A31-8 in each display image in FIGS. 21A and 21B.

In this way, the arrangement position of the list of the reference images included in the reference information group selected by the user is not limited to the lower end of the display image and can be the left end or the right end of the display image.

Here, the arrangement position of the list of the reference images can be determined according to information regarding reference images. For example, in a case where the reference images are images acquired in time series, it is only required to arrange the plurality of reference images in time series in the horizontal direction at the lower end of the display image. Furthermore, for example, in a case where the reference image is a slice image (MRI image or the like), it is only required to arrange the plurality of reference images in a sliced order in the vertical direction at the left end or the right end of the display image.

Figure 23:
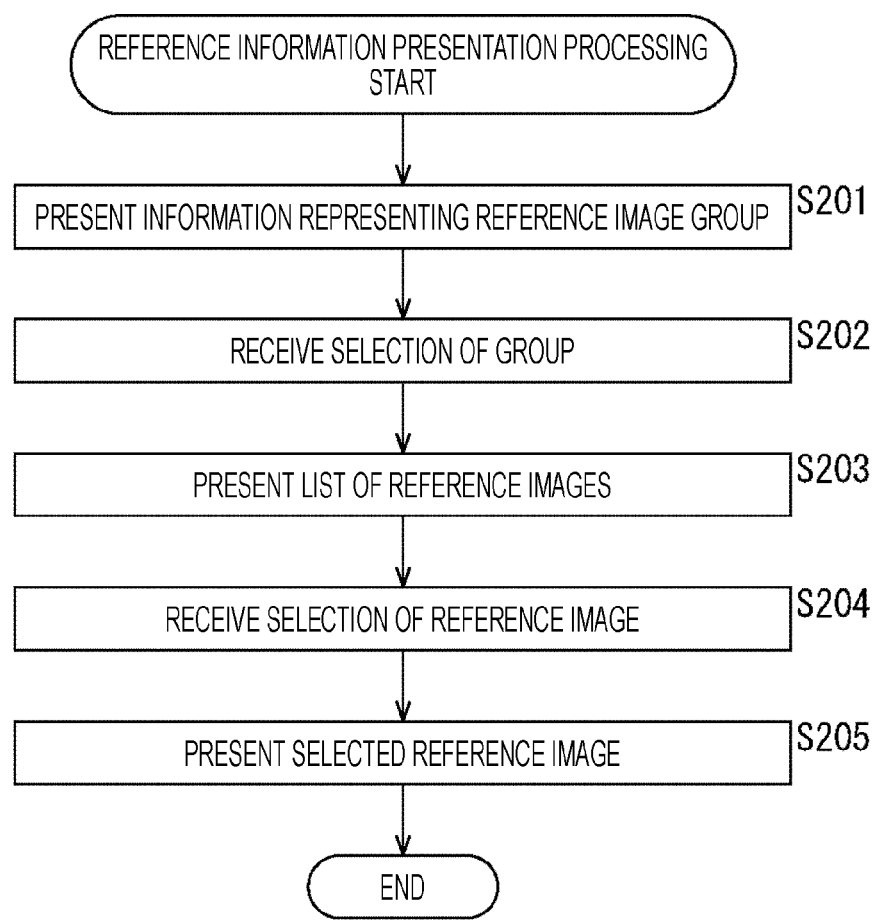
FIG. 23 is a flowchart for explaining reference information presentation processing of the control device.

Next, reference information presentation processing of the control device 12 will be described with reference to the flowchart in FIG. 23.

This reference information presentation processing is started when the user selects the item "Reference" in the operation menu.

In step S201, the acquisition unit 81 acquires a reference image from the external server 16 or the like. The acquired reference image is supplied to the control unit 82.

The control unit 82 arranges presented information in an upper portion of an operative field image and, for example, arranges thumbnail images of a reference information group on the left side and the right side of a display image so as to generate the display image having the region configuration in FIG. 14A. The control unit 82 outputs the display image to the display control unit 83. The display control unit 83 outputs the display image supplied from the control unit 82 to the display device 14 and makes the display device 14 present the reference information group.

In step S202, the control unit 82 receives selection of a thumbnail image of the reference information group by the user. For example, the control unit 82 detects a user's line-of-sight on the basis of a captured image supplied from a camera provided in the vicinity of the display device 14. The control unit 82 specifies the reference information group selected by the user on the basis of the detected user's line-of-sight.

In step S203, the control unit 82 generates the display image illustrated in the lower part of FIG. 17 by arranging the reference images included in the reference information group selected by the user on the lower side of the display image. The control unit 82 outputs the display image to the display control unit 83. The display control unit 83 outputs the display image supplied from the control unit 82 to the display device 14 and presents the list of the reference images included in the reference information group selected by the user.

In step S204, the control unit 82 receives selection of a reference image by the user. For example, the control unit 82 detects a user's line-of-sight on the basis of a captured image supplied from a camera provided in the vicinity of the display device 14. The control unit 82 specifies the reference image selected by the user on the basis of the detected user's line-of-sight.

In step S205, the control unit 82 generates the display image illustrated in the upper part of FIG. 18 by arranging the reference images selected by the user at the right end of the display image. The control unit 82 outputs the display image to the display control unit 83. The display control unit 83 outputs the display image supplied from the control unit 82 to the display device 14 and presents the reference images selected by the user.

Thus, the reference information presentation processing ends. Note that, in a case where the number of reference images included in the reference information group selected by the user is one, the processing in steps S203 and S204 is skipped.

According to the above processing, the control device 12 can present the presented information and display the operative field image and the reference image without disturbing concentration of the user.

4. Fourth Embodiment

In a case where an item "Move" in an operation menu is selected, a control device 12 executes display range change processing. A case where "Move" is selected will be described below.

Figure 24:
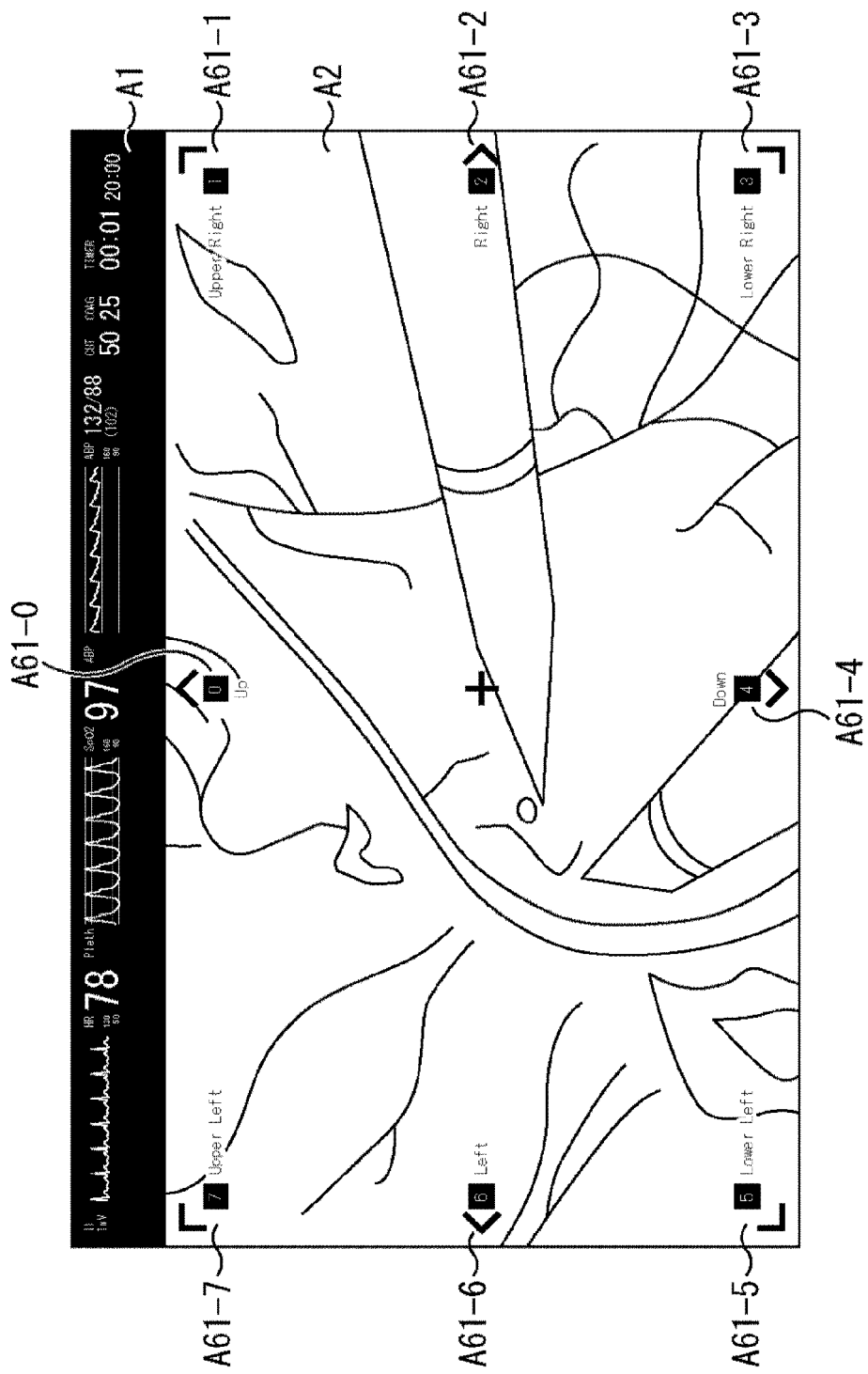
FIG. 24 is a diagram illustrating an example of a display image displayed on a display device 14 in a case where "Move" is selected.

FIG. 24 is a diagram illustrating an example of a display image displayed on a display device 14 in a case where "Move" is selected.

As illustrated in FIG. 24, the display image in a case where "Move" is selected is configured by arranging a presented information region A1 that is a narrow belt-like region on the upper side of an operative field image region A2 that is a region where an operative field image is displayed and arranging direction indicator regions A61-0 to A61-7 to be superimposed on the operative field image region A2.

Because the display image in FIG. 24 is similar to the display image described with reference to FIG. 2 except that the operation menu region A3 is not included and the direction indicator regions A61-0 to A61-7 are included, overlapped description will be appropriately omitted.

In the example in FIG. 24, the direction indicator regions A61-1, A61-3, A61-5, and A61-7 are respectively arranged at four corners of the operative field image region A2. The direction indicator region A61-0 is arranged at the center between the direction indicator regions A61-7 and A61-1, and the direction indicator region A61-2 is arranged at the center between the direction indicator regions A61-1 and A61-3. Furthermore, the direction indicator region A61-4 is arranged at the center between the direction indicator regions A61-3 and A61-5, and the direction indicator region A61-6 is arranged at the center between the direction indicator regions A61-5 and A61-7.

Each of the direction indicator regions A61-0 to A61-7 includes a display region of an indicator indicating a direction to which a display range of the displayed operative field image can be changed. In the example in FIG. 24, a name of the direction and a number indicating the direction are displayed as texts as a direction indicator. Moreover, an icon indicating the direction is displayed as a direction instruction. With these displays, the user is only required to intuitively recognize what operation should be performed next.

The user can select a direction indicator from among the direction indicators displayed in the direction indicator regions A61-0 to A61-7 with a line-of-sight or voice and change the display range of the operative field image toward the selected direction. That is, the direction indicators displayed in the direction indicator regions A61-0 to A61-7 indicate the directions to which an angle of view of the operative field image can be moved. When the angle of view is changed, a camera in a microscope device 11 may be driven, or image processing on a captured image imaged by the camera may be executed. Furthermore, in a case where predetermined voice (voice command) is input, the display image may have a configuration for displaying a predetermined mark at a user's line-of-sight position. Moreover, a following operation to make a predetermined mark be positioned at the center of the display image may be performed. For example, in a case where the user selects "Move" through voice input, the control device 12 displays the predetermined mark indicating the user's line-of-sight position in the display image and changes the display of the operative field image so that the predetermined mark is positioned at the center position of the display image.

In a case where there is a direction to which the display range of the operative field image cannot be changed, the control device 12 generates a display image in which only direction indicators that indicate directions to which the display range can be changed of the direction indicators displayed in the direction indicator regions A61-0 to A61-7 are displayed.

Figure 25A:
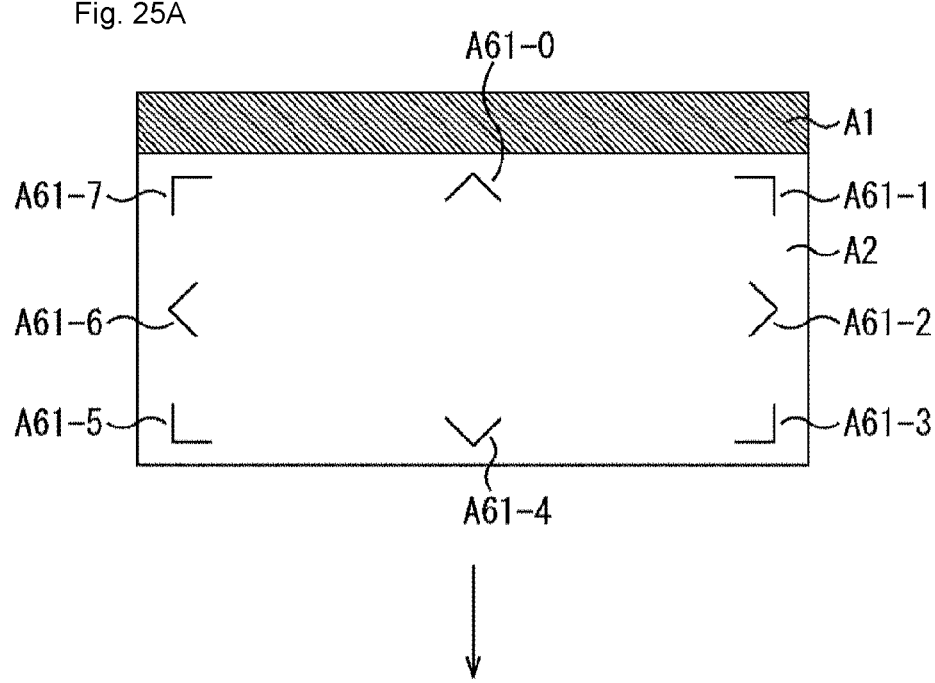
FIGS. 25A and 25B are diagrams illustrating an example of displayed direction indicators.
Figure 25B:
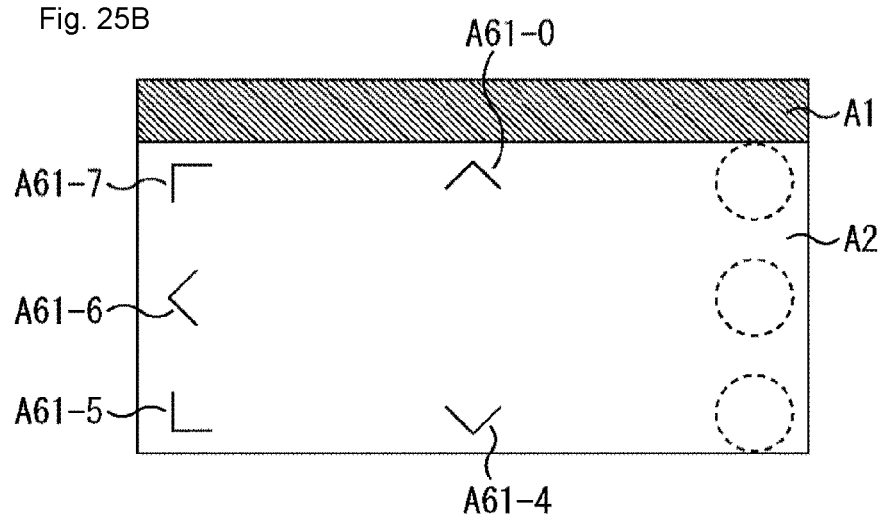

FIGS. 25A and 25B are diagrams illustrating an example of the displayed direction indicators.

As illustrated in the upper part of FIGS. 25A and 25B, in a case where there is no direction to which the display range of the operative field image cannot be changed, the display image is a display image in which the direction indicators are respectively displayed in the direction indicator regions A61-0 to A6-7.

For example, in a case where the direction indicator displayed in the direction indicator region A61-2 is selected by the user, an operative field image of which the display range is shifted rightward is displayed in the operative field image region A2. The display range may be changed by executing predetermined image processing on the operative field image supplied from the microscope device 11 or the display range of the operative field image may be changed by controlling the microscope device 11 by the control device 12.

Furthermore, for example, in a case where it is not possible to change the display range of the operative field image to a right direction, an oblique upper right direction, and an oblique lower right direction, as illustrated in the lower part pointed by an arrow in FIGS. 25A and 25B, the control device 12 generates a display image in which direction indicators are displayed in the direction indicator region A61-0 and the direction indicator regions A61-4 to A61-7.

Three dashed circles in the display image indicate that the direction indicators displayed in the direction indicator regions A61-1 to A61-3 are hidden. The direction indicators displayed in the direction indicator regions A61-1 to A61-3 are direction indicators that indicate the right direction, the oblique upper right direction, and the oblique lower right direction to which the display range cannot be changed.

As described above, the control device 12 presents the direction to which the display range of the displayed operative field image cannot be changed to the user by hiding the direction indicator indicating the direction. Here, display different from the direction indicator may indicate the direction to which the display range of the operative field image cannot be changed.

Figure 26A:
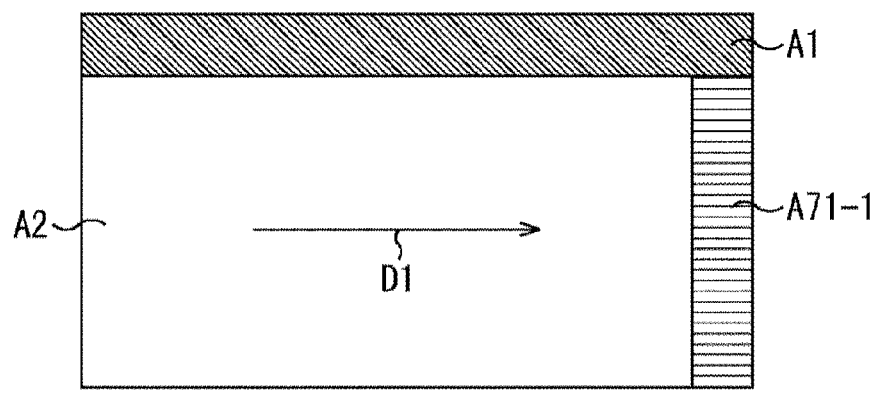
FIGS. 26A and 26B are diagrams illustrating an example of a region configuration of a display image presenting a direction to which a display range of an operative field image cannot be changed.
Figure 26B:
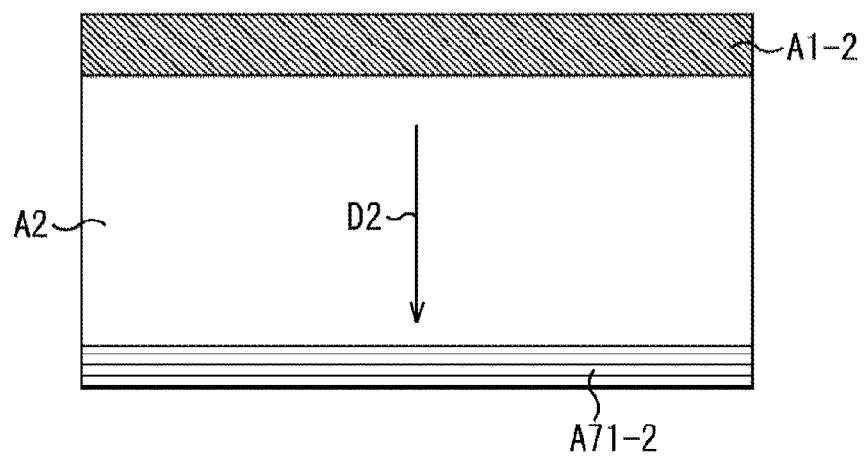

FIGS. 26A and 26B are diagrams illustrating an example of a region configuration of a display image presenting a direction to which a display range of an operative field image cannot be changed.

In FIGS. 26A and 26B, display images are illustrated in which arrangement positions of change limit information that is information indicating the direction to which the display range of the operative field image cannot be changed are different from each other. Because each display image in FIGS. 26A and 26B is similar to the display image described with reference to FIG. 2 except that the operation menu region A3 is not included and the display region of the change limit information is included, overlapped description will be appropriately omitted. The direction indicator regions A61-0 to A61-7 are arranged on the display images in FIGS. 26A and 26B, and direction indicators may be displayed in the respective regions.

In the example in FIG. 26A, a change limit information region A71-1 that is a display region of change limit information is arranged at the right end of the display image as a vertically-long region. In the change limit information region A71-1, for example, a monochrome image to which a predetermined luminance is set is displayed.

For example, as indicated by an arrow D1, the display image in FIG. 26A is generated by the control device 12 in a case where the display range of the operative field image is continuously changed rightward and it is not possible to change the display range of the operative field image in the right direction, the oblique upper right direction, and the oblique lower right direction.

In the example in FIG. 26B, a change limit information region A71-2 that is a display region of change limit information is arranged at the lower end of the display image as a narrow and long belt-like region. For example, as indicated by an arrow D2, the display image in FIG. 26B is generated by the control device 12 in a case where the display range of the operative field image is continuously changed downward and it is not possible to change the display range of the operative field image to the lower direction, the oblique lower left direction, and the oblique lower right direction.

Figure 27:
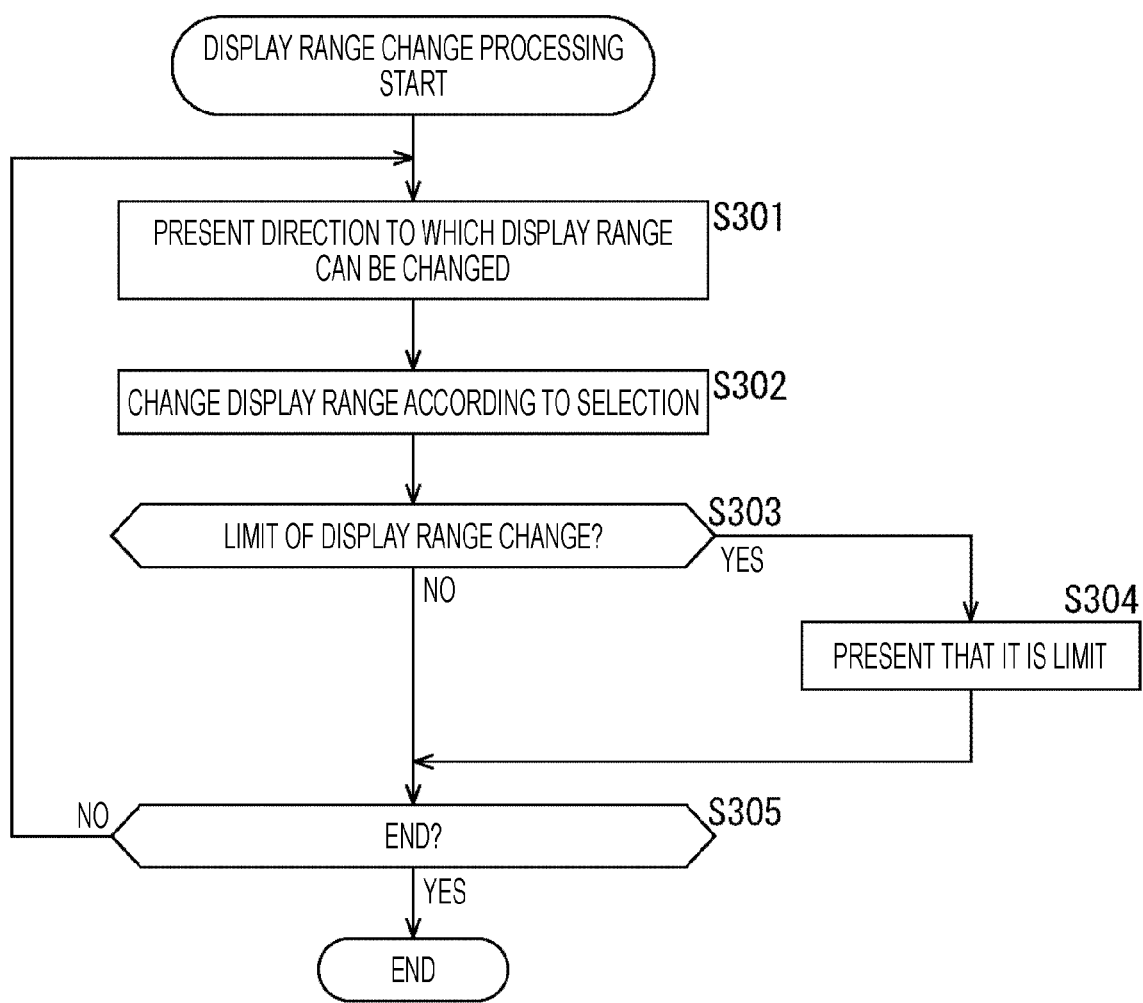
FIG. 27 is a flowchart for explaining display range change processing of the control device.

Next, display range change processing of the control device 12 will be described with reference to the flowchart in FIG. 27.

This display range change processing is started when the user selects an item "Move" in an operation menu.

In step S301, the control unit 82 arranges presented information in the upper portion of the operative field image and, for example, arranges direction indicators at four corners and center positions between the corners of the operative field image region A2 so as to generate the display image in FIG. 24. The control unit 82 outputs the display image to the display control unit 83. The display control unit 83 outputs the display image supplied from the control unit 82 to the display device 14 and presents a direction to which the display range of the operative field image can be changed.

In step S302, the control unit 82 receives selection of a direction indicator by the user. For example, the control unit 82 detects a user's line-of-sight on the basis of a captured image supplied from a camera provided in the vicinity of the display device 14. The control unit 82 specifies the direction indicator selected by the user on the basis of the detected user's line-of-sight.

The control unit 82 generates a display image, of which the display range of the operative field image has been changed, according to the direction indicator selected by the user. The control unit 82 outputs the display image to the display control unit 83. The display control unit 83 outputs the display image supplied from the control unit 82 to the display device 14 and displays the display image of which the display range of the operative field image has been changed.

In step S303, the control unit 82 determines whether or not it is a limit to change the display range.

In a case where it is determined in step S303 that it is the limit to change the display range, the procedure proceeds to step S304.

In step S304, for example, the control unit 82 generates a display image in which only the direction indicators, among the direction indicators, of the directions to which the display range of the operative field image can be changed are arranged. The control unit 82 outputs the display image to the display control unit 83. The display control unit 83 outputs the display image supplied from the control unit 82 to the display device 14 and, as illustrated in FIG. 25B, presents that it is the limit to change the display range of the operative field image. Furthermore, as illustrated in FIGS. 26A and 26B, the change limit information may be displayed in the direction to which the display range of the operative field image cannot be changed.

In step S305, the control unit 82 determines whether or not to end the display range change processing on the basis of the selection by the user. Note that, in a case where it is determined in step S303 that it is not the limit to change the display range of the operative field image, step S304 is skipped, and the procedure proceeds to step S305. Then, it is determined whether or not to end the display range change processing on the basis of the selection by the user.

In a case where it is determined in step S305 not to end the display range change processing, the procedure returns to step S301, and the subsequent processing is executed.

On the other hand, in a case where it is determined in step S305 to end the display range change processing, the display range change processing ends.

According to the above processing, the control device 12 can present the presented information and can change the display range of the operative field image without disturbing concentration of the user.

5. Modification

Example of Display Position Adjustment with Work Concentration Region

The control device 12 obtains a point of regard on the basis of a user's line-of-sight detected on the basis of a captured image supplied from the camera provided in the vicinity of the display device 14. At this time, the control device 12 may obtain a predetermined work concentration region on the basis of a distribution of the point of regard.

The work concentration region is a region in a display image that is assumed that the user concentrates the line-of-sight. Here, a region, of which a change within a predetermined time is larger than a predetermined amount, among the regions included in the operative field image may be obtained as a work concentration region in which a large movement is made.

Furthermore, an alert may be displayed at a predetermined position in the display image on the basis of the obtained work concentration region.

Figure 28A:
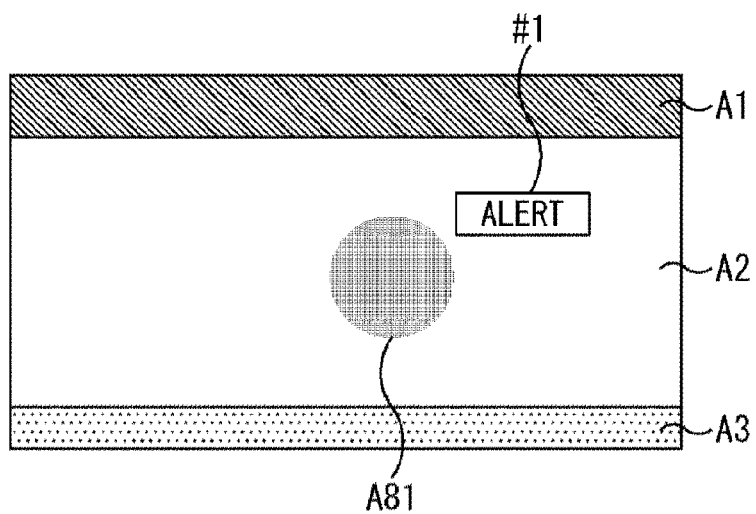
FIGS. 28A and 28B are diagrams illustrating an example of a region configuration of a display image in which an alert is displayed.
Figure 28B:
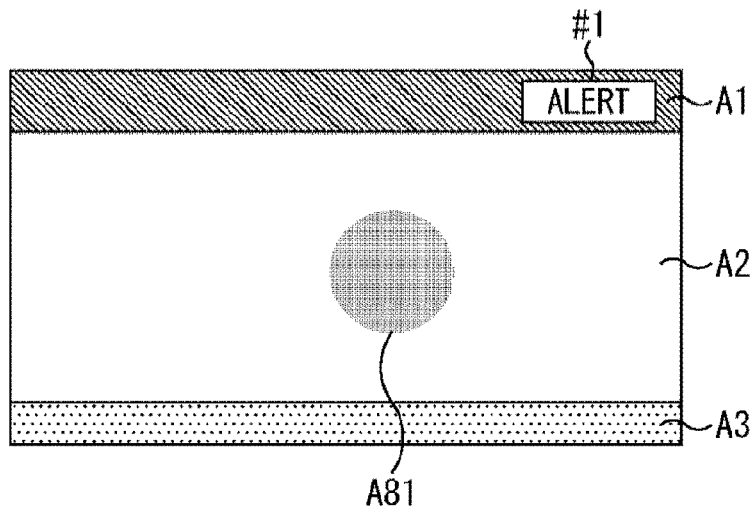

FIGS. 28A and 28B are diagrams illustrating an example of a region configuration of a display image in which an alert is displayed.

Because each display image in FIGS. 28A and 28B is similar to the display image described with reference to FIG. 2 except that an alert is displayed, overlapped description will be appropriately omitted.

In the example in FIG. 28A, a work concentration region A81 is obtained by the control device 12 as a circular region at the substantially center in the operative field image region A2. In the example in FIG. 28A, an alert #1 is arranged in the vicinity of the work concentration region A81. Furthermore, the alert #1 is arranged to be superimposed on the operative field image region A2.

The alert #1 is displayed on the basis of information such as the monitoring information. Furthermore, the alert #1 may be displayed as setting a predetermined transmittance. Note that the work concentration region A81 is displayed for convenience of description and is not actually displayed.

In the example in FIG. 28B, unlike the alert #1 in A of FIG. 28A, the alert #1 is arranged in the presented information region A1. In this case, the alert #1 is displayed in the presented information region A1 similarly to the presented information such as the monitoring information displayed in the presented information region A1.

In this way, the alert #1 can be arranged at any position in the display image. Furthermore, another piece of information based on the monitoring information or the like may be displayed similarly to the alert #1.

Furthermore, an arrangement position of the information arranged to be superimposed on the operative field image region A2 may be determined on the basis of the obtained work concentration region. For example, the arrangement position of the selection reference image region described in the third embodiment may be determined on the basis of the work concentration region.

Figure 29A:
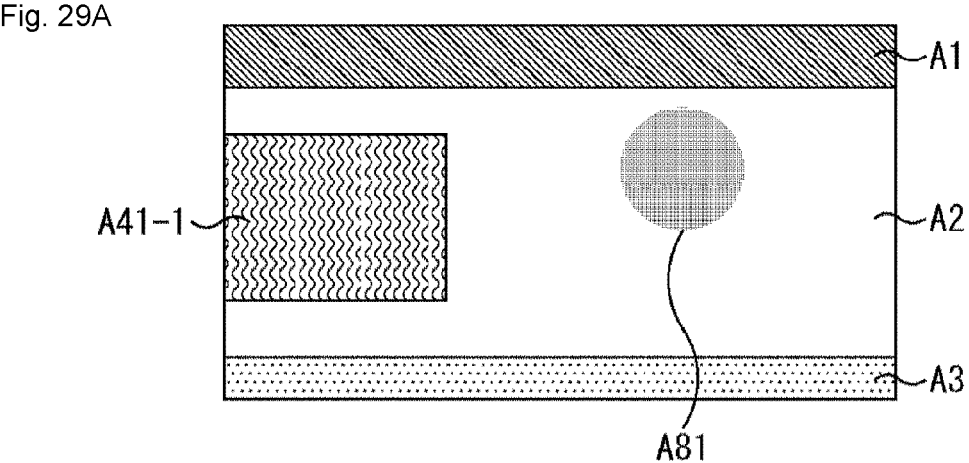
FIGS. 29A and 29B are diagrams illustrating another example of the region configuration of the display image in which the selected reference image is displayed.
Figure 29B:
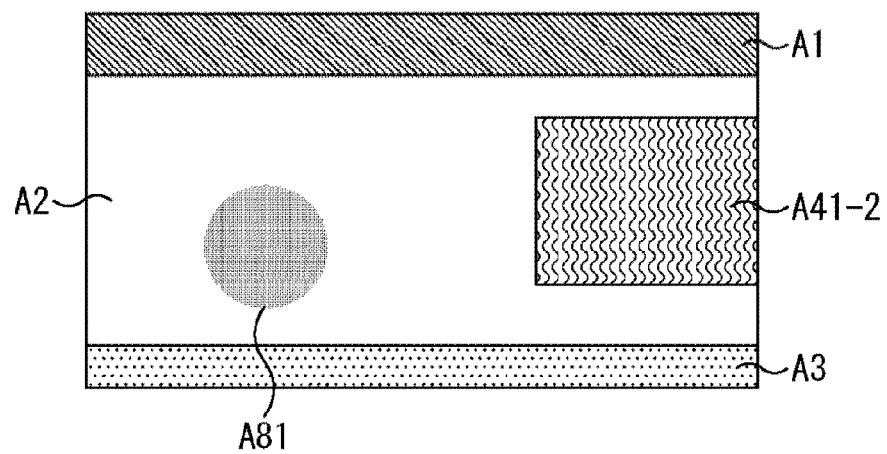

FIGS. 29A and 29B are diagrams illustrating another example of the region configuration of the display image in which the selected reference image is displayed.

Because a display image in FIG. 29A is similar to the display image described with reference to the upper part of FIG. 18 except that the arrangement positions of the selected image regions are different from each other, overlapped description will be appropriately omitted.

In the example in FIG. 29A, a circular region on the upper right side of the display image is the work concentration region A81. The control device 12 arranges the selection reference image region A41 at one of the left end or the right end of the display image apart from the work concentration region A81. In the example in FIG. 29A, a reference image region A41-1 that is a display region of a reference image selected by a user is arranged at the left end of the display image.

In the example in FIG. 29B, a circular region on the lower left side of the display image is the work concentration region A81. In the example in FIG. 29B, a selection reference image region A41-2 that is a display region of a reference image selected by a user is arranged at the right end of the display image to be symmetrical with respect to the selection reference image region A41-1 in the display image in FIG. 29A.

In this way, it is possible to arrange the information arranged to be superimposed on the operative field image region A2 at the position determined on the basis of the work concentration region.

Example of All-Clear Operation

A user can control a region configuration of a display image by performing a predetermined operation. For example, the user can display the display image described with reference to FIG. 2 by performing a line-of-sight, voice, gesture, touch operation or the like. Furthermore, for example, the user can display a display image including only the operative field image region A2 by performing the similar operation.

Here, the display image including only the operative field image region A2 may be displayed by pressing a button displayed in the display image.

Figure 30A:
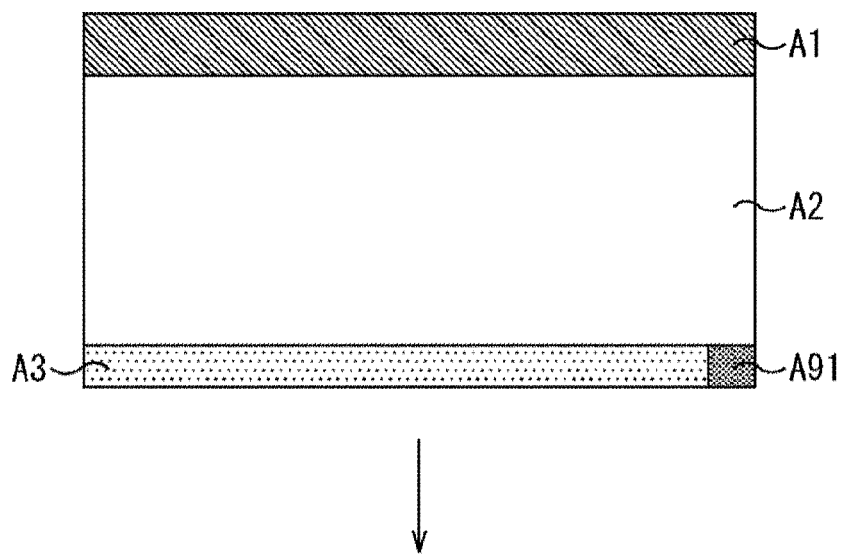
FIGS. 30A and 30B are diagrams illustrating an example of a region configuration of a display image in which a button is displayed.
Figure 30B:
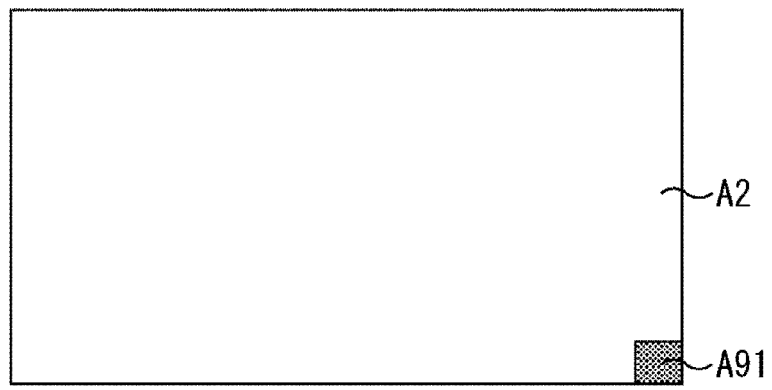

FIGS. 30A and 30B are diagrams illustrating an example of a region configuration of a display image in which a button is displayed.

Because a display image in the upper part of FIGS. 30A and 30B is similar to the display image described with reference to FIG. 2 except that a button is arranged, overlapped description will be appropriately omitted.

In the example in the upper part of FIGS. 30A and 30B, a button region A91 that is a display region of a button is arranged at a lower right corner of the display image to be superimposed on the operation menu region A3 as a substantially square region. The user can display the display image in the lower part pointed by an arrow in FIGS. 30A and 30B by pressing the button displayed in the button region A91.

In the display image in the lower part of FIGS. 30A and 30B, the operative field image region A2 is arranged in the entire screen, and only the operative field image is displayed.

As described above, the user can switch a display image in a certain state to a display image in an initial state (display image in FIG. 2, display image in FIG. 30B, or the like) with one action by performing the predetermined operation.

Example of Case where "Zoom" is Selected

In a case where an item "Zoom" in the operation menu is selected, the control unit 82 generates a display image in which the operative field image region A2 is divided.

Figure 31:
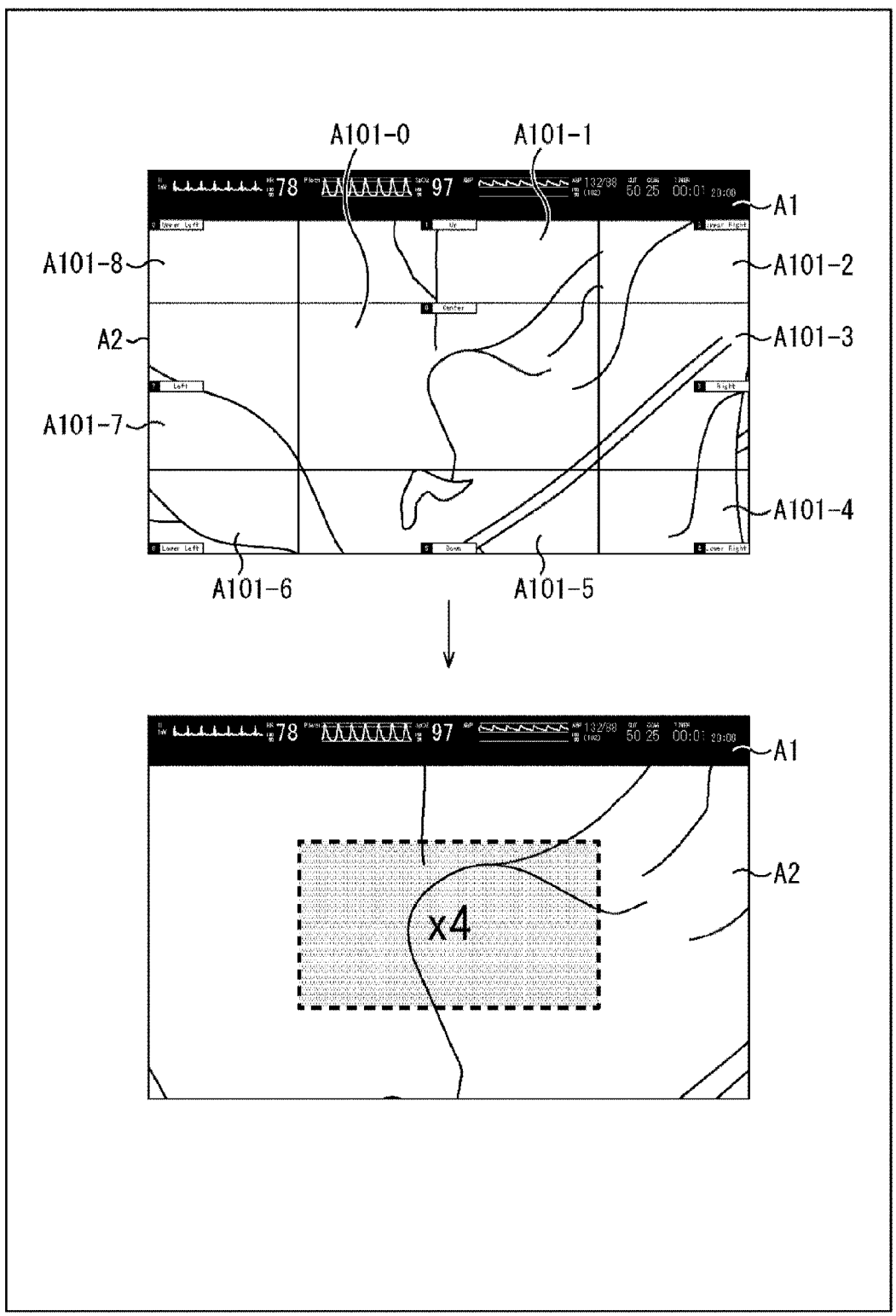
FIG. 31 is a diagram illustrating an example of a display image displayed on the display device in a case where "Zoom" is selected.

FIG. 31 is a diagram illustrating an example of a display image displayed on the display device 14 in a case where "Zoom" is selected.

As illustrated in the upper part of FIG. 31, the display image in a case where "Zoom" is selected is configured by arranging the presented information region A1 that is a narrow belt-like region on the upper side of the operative field image region A2. The operative field image region A2 includes rectangular operative field image divided regions A101-0 to A101-8.

The operative field image divided region A101-0 is a region arranged at the center of nine regions, arranged as 3×3 (vertical×horizontal) obtained by dividing the operative field image region A2. The operative field image divided regions A101-1 and A101-5 are respectively arranged on the upper side and the lower side of the operative field image divided region A101-0 and are rectangular regions having the same width and the same height. The operative field image divided regions A101-2, A101-4, A101-6, and A101-8 are arranged at respective corners of the operative field image region A2 and are rectangular regions having the same width and the same height. The operative field image divided regions A101-3 and A101-7 are respectively arranged on the right side and the left side of the operative field image divided region A101-0 and are rectangles having the same width and the same height.

Note that, in the example in the upper part of FIG. 31, an example of a case where sizes of the respective operative field image divided regions are not the same has been described. However, the sizes of all the operative field image divided regions may be equal to each other.

In the operative field image divided regions A101-0 to A101-8, the operative field image displayed in the operative field image region A2 is divided and displayed. Furthermore, in the operative field image divided regions A101-0 to A101-8, a number indicating each region and a name of each region are displayed at predetermined positions in each region.

The user can select the divided operative field images displayed in the operative field image divided regions A101-0 to A101-8 with the line-of-sight or voice. For example, in a case where the divided operative field image displayed in the operative field image divided region A101-0 is selected, the control device 12 generates the display image in the lower part pointed by an arrow in FIG. 31.

In the display image in the lower part of FIG. 31, the operative field image displayed in the operative field image divided region A101-0 is enlarged fourfold and displayed in the operative field image region A2. A dashed rectangle represents a region corresponding to the operative field image divided region A101-0.

In a case where the user selects the operative field image displayed in the operative field image divided region, the control unit 82 enlarges the operative field image displayed in the region selected by the user at a predetermined magnification ratio and arranges the operative field image in the operative field image region A2. The magnification ratio at which the operative field image is enlarged may be designated by a line-of-sight or voice after the user selects the operative field image displayed in the operative field image divided region.

Example of Operation in Response to Combination of Line-of-Sight and Voice

The user can select information to be displayed by combining a plurality of inputs such as a line-of-sight or voice. For example, the user can select the thumbnail image of the reference information group described in the third embodiment by combining a line-of-sight and voice.

Figure 32:
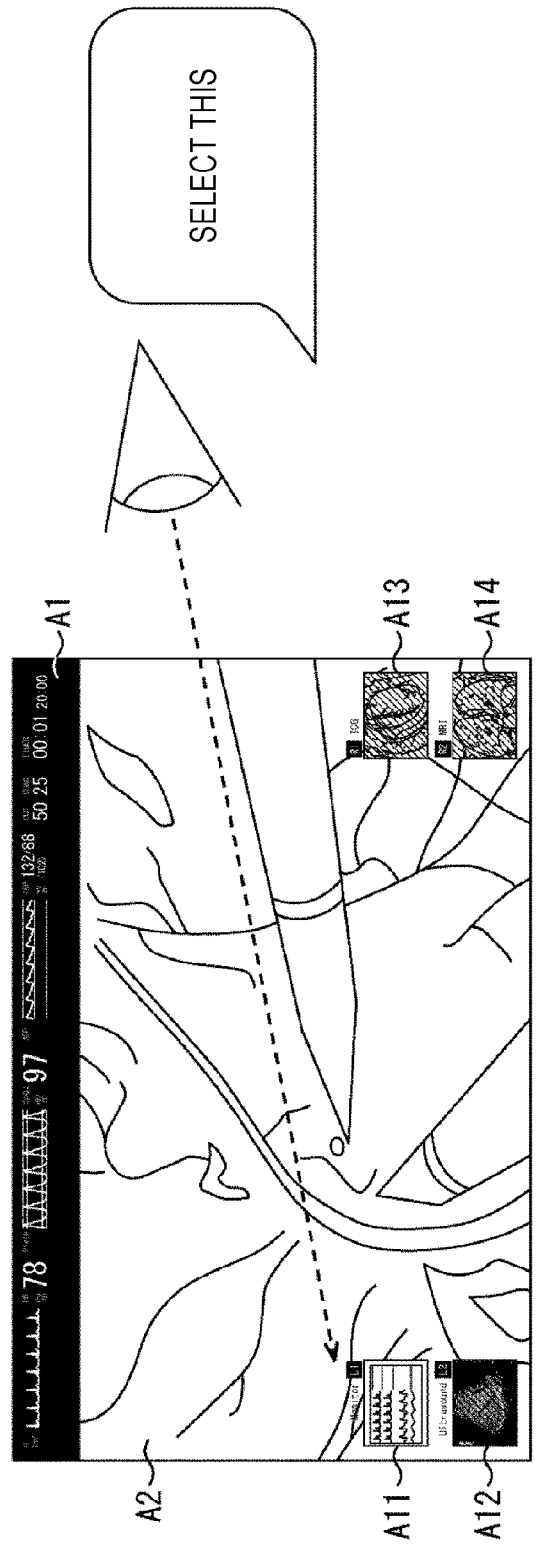
FIG. 32 is a diagram illustrating an example of an operation performed in response to a combination of a line-of-sight and voice.

FIG. 32 is a diagram illustrating an example of an operation performed in response to a combination of a line-of-sight and voice.

In the example in FIG. 32, a user's line-of-sight is directed to a thumbnail image displayed in the reference information group region A11. This line-of-sight is a line-of-sight detected by the control device 12 on the basis of the captured image supplied from the camera provided in the vicinity of the display device 14.

The thumbnail image displayed in the reference information group region A11 to which the line-of-sight is directed is similar to the display image described with reference to FIG. 15. In the example in FIG. 32, hatched thumbnail images displayed in the reference information group regions A12 to A14 indicate that the thumbnail images are displayed as setting a predetermined transmittance.

In this way, the control unit 82 sets a transmittance to a thumbnail image other than the thumbnail image to which the detected user's line-of-sight is directed among the thumbnail images displayed in the reference information group regions A11 to A14 and generates a display image. That is, while the transmittance is not set to the focused thumbnail image to which the user's line-of-sight is directed, the transmittance is set to the thumbnail image other than the above thumbnail image.

Then, after confirming that the thumbnail image, to which the line-of-sight is directed is focused, the user can select the thumbnail image to which the line-of-sight is directed with predetermined voice (voice command) such as "select this".

Furthermore, the thumbnail image may be focused on the basis of the region to which the user's line-of-sight is directed.

Figure 33:
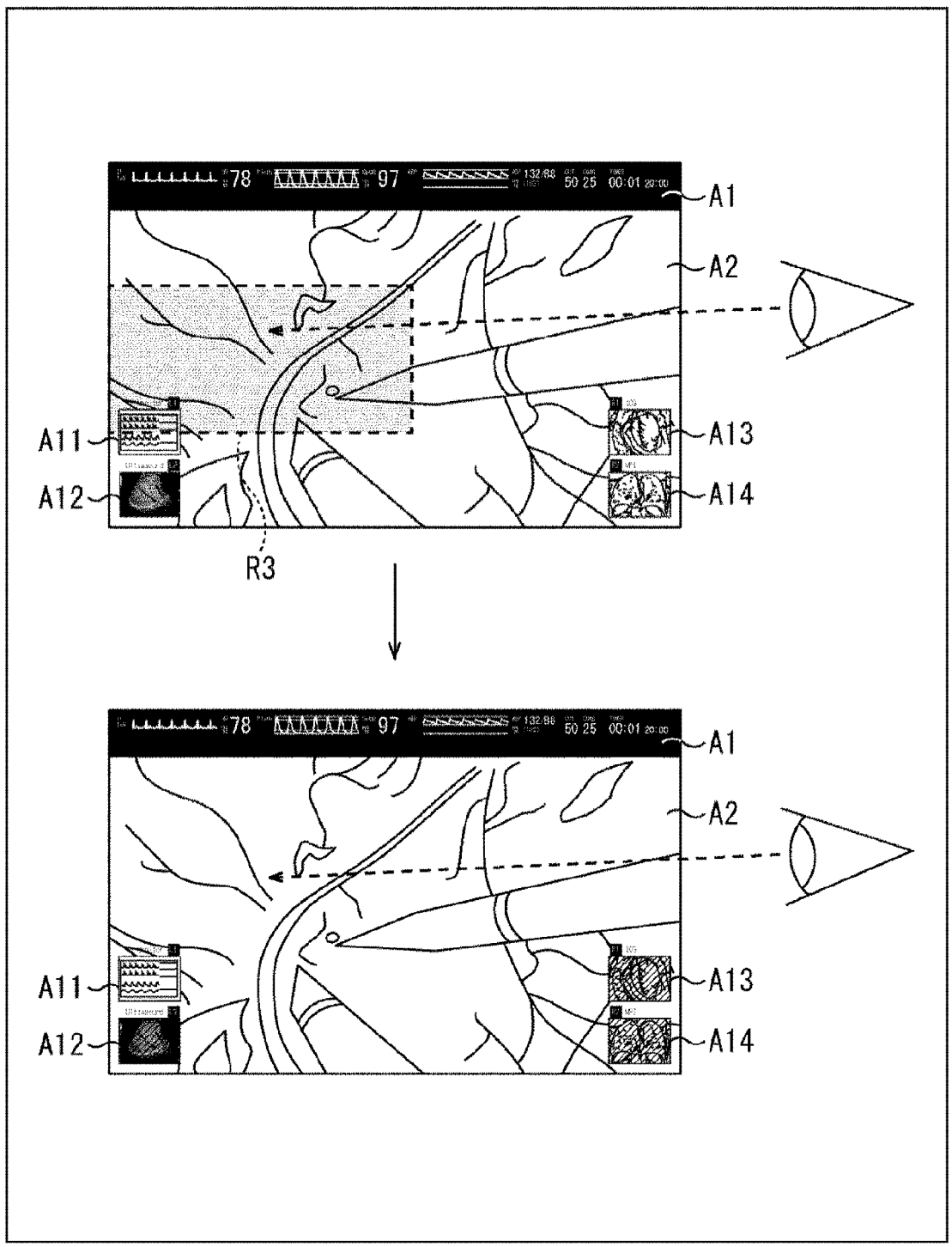
FIG. 33 is a diagram illustrating an example of a display image in which a thumbnail image is focused on the basis of a region to which a user's line-of-sight is directed.

FIG. 33 is a diagram illustrating an example of a display image in which a thumbnail image is focused on the basis of a region to which a user's line-of-sight is directed.

In the example in the upper part of FIG. 33, the user's line-of-sight is directed to the vicinity of the thumbnail image in the reference information group region A11. At this time, the control unit 82 determines, for example, a rectangular region R3 surrounded by a dashed line as the region to which the user's line-of-sight is directed, on the basis of the user's line-of-sight. Because the rectangular region R3 surrounded by the dashed line includes only a part of the reference information group region A11 of the reference information group regions A11 to A14, the control unit 82 generates a display image illustrated in the lower part pointed by an arrow in FIG. 33.

The display image in the lower part of FIG. 33 is similar to the display image described with reference to FIG. 32. That is, the control unit 82 does not set the transmittance to the thumbnail image included in the region to which the user's line-of-sight is directed and sets the transmittance to the thumbnail image other than the above thumbnail image and generates a display image. Then, after confirming the focused thumbnail image, the user can select the thumbnail image with predetermined voice.

Note that the user can select the focused thumbnail image with the predetermined voice without directing the line-of-sight to the thumbnail image.

Figure 34:
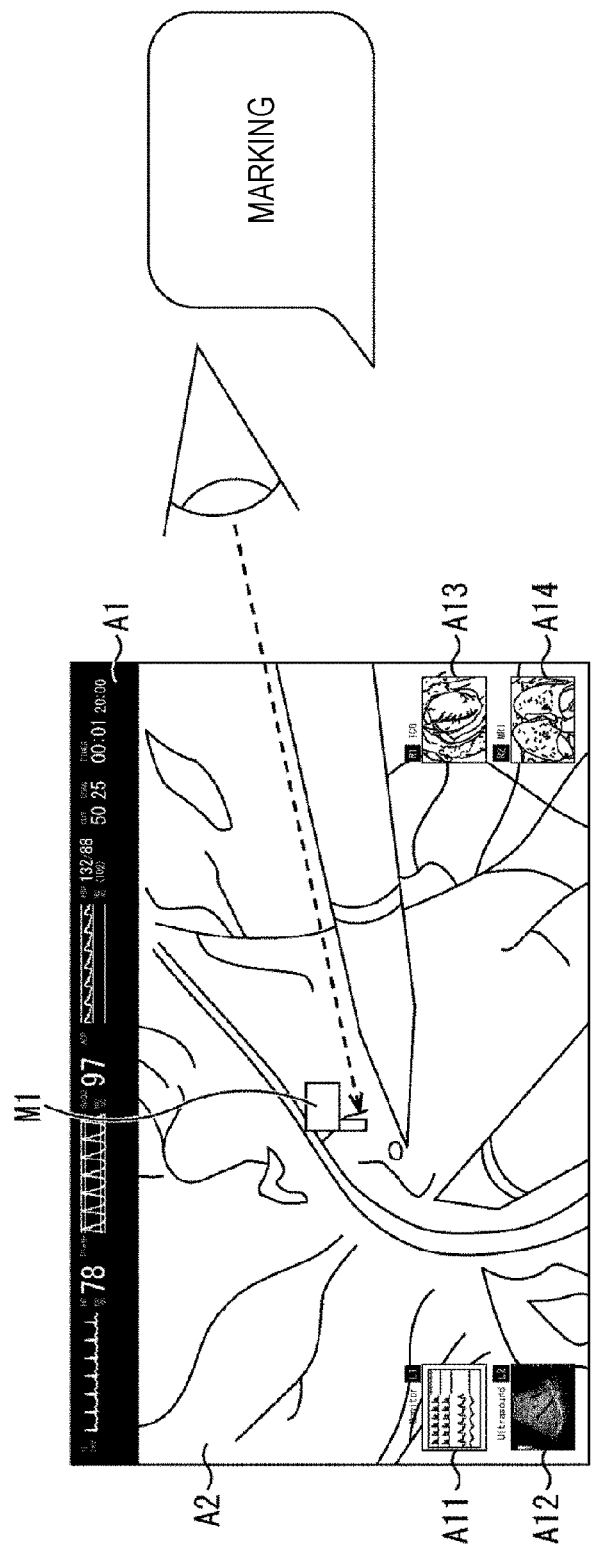
FIG. 34 is a diagram illustrating another example of the operation performed in response to the combination of the line-of-sight and the voice.

FIG. 34 is a diagram illustrating another example of the operation in response to the combination of the line-of-sight and the voice.

In the example in FIG. 34, the user's line-of-sight is directed to a position at the substantially center of the operative field image region A2. In the display image in FIG. 34, a marking M1, which is a flag icon, is displayed at the position in the operative field image region A2 to which the user's line-of-sight is directed. Here, in a case where the user utters predetermined voice such as "marking" while directing a line-of-sight, the control device 12 generates a display image in which the marking M1 is superimposed and arranged at the position to which the user's line-of-sight is directed.

Furthermore, a display image displayed after the predetermined voice (voice command) is input may have a configuration in which a position of the user's line-of-sight is displayed as a predetermined mark in a screen. For example, in a case where the user selects "Move" illustrated in FIG. 4 through voice input, the control device 12 displays a mark that follows the position of the detected user's line-of-sight in the screen. At this time, the control device 12 may change the display range of the operative field image following the position of the mark so that the position of the mark overlaps the center position of the image.

Furthermore, presented information displayed in the presented information region A1 (header region) may include time information that includes a total surgery time counted from a time when an operation is started, as illustrated in FIG. 35. Furthermore, the presented information may include alert information, a setting value of a pneumoperitoneum device, a setting value of an electrocautery, and information indicating a timer. As the information indicating the timer, for example, it is preferable to display a setting time and a count-up time and change a color of characters and display the characters when the count-up time reaches the setting time. Furthermore, the control device 12 may display content to be alerted as the alert information.

Furthermore, an operation menu displayed in the operation menu region A3 (footer region) may be the operation menu illustrated in FIG. 36. In the example in FIG. 36, texts of "Camera", "Reference", "Timer Start", "Screen", and "Others" representing option items that can be selected by a user are displayed. "Camera" is an item that is used to make the control device 12 control a medical imaging device that captures an operative field image or control display of an operative field image. "Timer Start" is an item that is used to make the control device 12 start counting of a count-up timer. "Reference" is an item similar to "Reference" in the embodiment described above. "Screen" is an item that is used to make the control device 12 switch a display state. The switching of the display state is, for example, switching between display and non-display of a user interface or switching between ON/OFF of a full screen display of a reference image. "Others" is an item that is used to make the control device 12 perform other behaviors such as display of a submenu or the like. Note that the control device 12 may display "Cancel" that is an item used to cancel content instructed by the user to the control device 12.

Figure 37:
FIG. 37 is an enlarged view illustrating the operation menu region.

Furthermore, when "Camera" is selected, an item of the operation menu displayed in the operation menu region A3 is changed to an item that is used to control a medical imaging device or control display of an operative field image. In the example in FIG. 37, texts of "Zoom In", "Zoom Out", "Zoom Reset", "Center", "Move", and "Cancel" representing option items that can be selected by the user are displayed. "Zoom In" is an item that is used to make the control device 12 perform control for increasing a magnification of an operative field image. "Zoom Out" is an item that is used to make the control device 12 perform control for decreasing the magnification of the operative field image. "Zoom Reset" is an item that is used to make the control device 12 perform control for returning the magnification of the operative field image to a prescribed value, and "Center" is an item that is used to make the control device 12 perform control for aligning the center of the operative field image on the center of the display device. "Move" is an item similar to "Move" in the embodiment described above. "Cancel" is an item that is used to make the control device 12 cancel content instructed by the user to the control device 12 in the past.

Note that, when "Zoom In" or "Zoom Out" is selected by the user, it is preferable to detect a user's line-of-sight at the time of the selection and change the display region of the operative field image so that the line-of-sight position is positioned at the center.

Figures 38A, 38B:
FIGS. 38A and 38B are diagrams illustrating an example of a lower region of a selection reference image region in which an operation item is displayed.

Furthermore, when the reference image is displayed, the control device 12 may display an operation item that makes the display device 12 perform control for displaying the reference image in the lower regions of the selection reference image regions A41 and A42. As illustrated in FIG. 38A, when a plurality of reference images is displayed, it is preferable to display the operation item in the lower region of the selection reference image region in which each reference image is displayed. As illustrated in FIG. 38B, the operation item is, for example, "Enlarge" that performs control for largely displaying an image or "Close" for canceling the display of the reference image. Note that the control device 12 may display "Full Size" that displays the reference image across the entire display region and "Half Size" that displays the reference image in a half region of the display region in the lower region of the selection reference image region as operation items. Furthermore, when the plurality of reference images is displayed, a reference image that controls display may be selected on the basis of the user's line-of-sight. Furthermore, the control device 12 may display a lower region of a reference image of which the display region overlaps a position of the detected user's line-of-sight (selected reference image) to be darker than a lower region of another reference image (unselected reference image). As a result, the control device 12 can present a reference image to be an operation target of voice control to the user.

Figure 39:
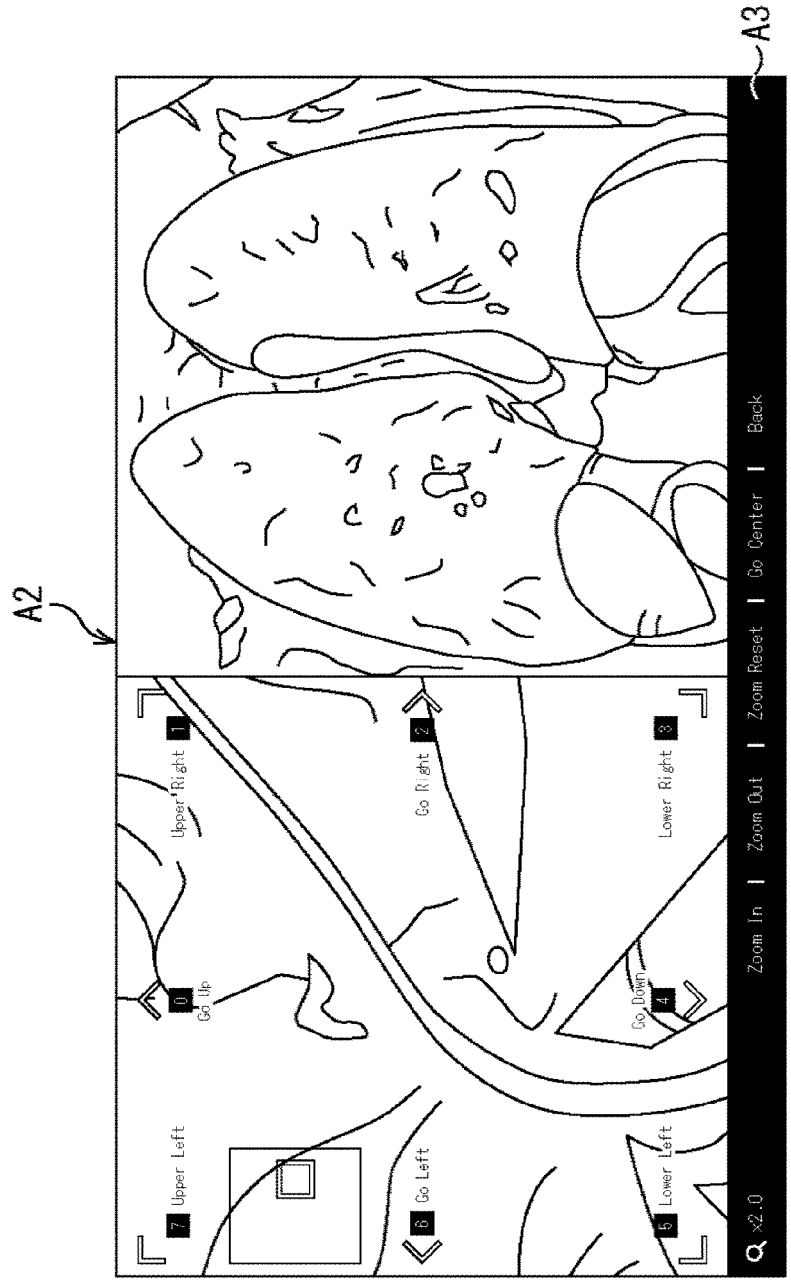
FIG. 39 is a diagram illustrating an example of a display image in which an image is displayed in each region obtained by dividing an operative field image region.

Furthermore, as in FIG. 39, the control device 12 may have a configuration in which the operative field image region A2 is divided into two regions in the horizontal direction in response to an instruction of a user, an operative field image is displayed in one of the divided regions, and a reference image and an operative field image enlarged with a predetermined magnification ratio are displayed in another region. Note that the item of "Half Size" may be added to the items in the operation menu as an item used to instruct the control device 12 to divide a display region by a user. Furthermore, when the user selects "Half Size", an item "Cancel Half Size" may be added to the items in the operation menu as an item that is used to make the control device 12 cancel the instruction to divide the region.

Note that it is possible to arrange any image at a position to which the user's line-of-sight is directed. The image to be arranged may be determined on the basis of user's voice. Furthermore, here, as line-of-sight region corresponding processing regarding a line-of-sight region according to the user's line-of-sight, processing for selecting a selection target according to user's voice in a case where the selection target exists in the line-of-sight region, processing for marking a position indicated by the line-of-sight region according to the user's voice, or processing for focusing on the selection target in the line-of-sight region is exemplified. However, another processing may be executed.

Others

A program executed by the control device 12 may be a program in which processing is executed along the order described herein in a time series manner and a program in which the processing is executed in parallel or at a necessary timing, for example, when a call has been performed.

The above-mentioned series of processing can be performed by hardware and software. In a case where the software executes the series of processing, a program included in the software is installed to a computer in which the software included in the software is incorporated in dedicated hardware, a general-purpose personal computer, or the like.

The program to be installed is provided by recording the program in a removable recording medium 61 illustrated in FIG. 7 including an optical disk (compact disc-read only memory (CD-ROM), digital versatile disc (DVD), or the like), a semiconductor memory, or the like. Furthermore, the program may be provided via a wired or wireless transmission medium such as a local area network, the Internet, or digital broadcasting. The program may be installed to the ROM 52 or the recording unit 58 in advance.

Note that, the program performed by the computer may be a program in which processing is executed along the order described herein in a time series manner or a program in which the processing is executed in parallel or at a necessary timing, for example, when a call has been performed.

Note that, a system means herein an assembly of a plurality of components (devices, modules (parts), and the like), and it is not considered whether or not all the components are in the same housing. Therefore, both of a plurality of devices respectively housed in different housings from each other and connected via the network and a single device having a plurality of modules housed in one housing are systems.

Note that the effects described in the present specification are only exemplary and not limited to these. Furthermore, there may be an additional effect.

The embodiment of the present technology is not limited to the above-mentioned embodiments, and various changes can be made without departing from the scope of the present technology.

For example, the present technology may have a configuration of cloud computing in which a single function is shared and separately performed in cooperation by a plurality of devices via a network.

Furthermore, each step described with reference to the above-mentioned flowchart can be performed by a single device or can be divided and performed by a plurality of devices.

Moreover, in a case where a plurality of kinds of processing is included in one step, the plurality of kinds of processing included in one step can be executed by a single device or can be divided and executed by a plurality of devices.

<Example of Combination of Configurations>

The present technology can have the following configurations.

(1)

A medical display system including:
a control device including
an acquisition unit that acquires an operative field image signal generated by a medical imaging device that images an operative field of a patient and a presented information signal generated by a device that includes an external device excluding the medical imaging device, and
a control unit that generates a display image on the basis of the operative field image signal and the presented information signal, in which
the control unit generates the display image by arranging and displaying presented information generated from the presented information signal in an upper region of a display region of the display image, arranging and displaying an operative field image generated on the basis of the operative field image signal in a middle region that has a length equivalent to the upper region in a horizontal direction, and arranging and displaying user interface information used to control the control device in a region on a lower side of the upper region.

(2)

The medical display system according to (1), in which
the presented information includes at least monitoring information generated from a monitoring information signal acquired from a monitoring device that monitors biological information of the patient.

(3)

The medical display system according to (2), in which
the control unit arranges the presented information in a predetermined display form including a text or a graph.

(4)

The medical display system according to (2) or (3), in which
the presented information includes information regarding surgical instruments.

(5)
The medical display system according to any one of (2) to (4), in which
the presented information includes information regarding a time.

(6)
The medical display system according to any one of (2) to (5), in which
the presented information includes information that changes in real time.

(7)
The medical display system according to any one of (1) to (6), in which
the operative field image includes an image that changes in real time.

(8)
The medical display system according to any one of (1) to (7), in which
the region on the lower side of the upper region includes a lower region that has a length equivalent to the upper region in the horizontal direction, and
the control unit arranges the user interface information in the lower region.

(9)
The medical display system according to any one of (1) to (7), in which
the region on the lower side of the upper region includes a region that has a length different from the upper region in the horizontal direction and includes a left and right portion region corresponding to at least one of regions at a left end or a right end of the middle region, and
the control unit arranges the user interface information in the left and right portion region.

(10)
The medical display system according to any one of (1) to (9), in which
the control unit changes a method for displaying the presented information arranged in the upper region on the basis of information regarding a user.

(11)
The medical display system according to (10), in which
the information regarding the user includes information regarding a user's line-of-sight or information according to an operation or a behavior by the user.

(12)
The medical display system according to any one of (1) to (11), in which
the control unit arranges one or a plurality of captured images generated by another medical imaging device different from the medical imaging device in the region on the lower side of the upper region.

(13)
The medical display system according to (12), in which
the control unit
arranges a thumbnail image corresponding to a reference image that is a captured image for reference,
aligns and arranges a plurality of reference images corresponding to the selected thumbnail image in a predetermined direction in a case where the thumbnail image is selected, and
arranges a reference image obtained by enlarging the selected reference image in a case where a desired reference image is selected from among the plurality of reference images.

(14)
The medical display system according to any one of (1) to (11), in which
the control unit arranges a direction indicator used to change a display range of the operative field image in the region on the lower side of the upper region.

(15)
The medical display system according to any one of (1) to (14), in which
the control unit
specifies a work concentration region in the operative field image on which a user's line-of-sight is concentrated, and
determines an arrangement position of information to be superimposed on the operative field image on the basis of the specified work concentration region.

(16)
The medical display system according to (15), in which
the control unit determines the arrangement position so that an alert or information for reference is arranged in a region excluding the work concentration region.

(17)
The medical display system according to any one of (1) to (16), in which
the control unit
detects a user's line-of-sight with respect to the middle region, and
executes line-of-sight region corresponding processing regarding a line-of-sight region according to the detected line-of-sight.

(18)
The medical display system according to (17), in which
in a case where a selection target exists in the line-of-sight region, the line-of-sight region corresponding processing includes processing for selecting the selection target according to voice of the user, processing for marking at a position indicated by the line-of-sight region according to the voice of the user, and processing for focusing on the selection target in the line-of-sight region.

(19)
A control device including:
an acquisition unit configured to acquire an operative field image signal generated by a medical imaging device that images an operative field of a patient and a presented information signal generated by a device that includes an external device excluding the medical imaging device; and
a control unit configured to generate a display image on the basis of the operative field image signal and the presented information signal, in which the control unit generates the display image by arranging
and displaying presented information generated from the presented information signal in an upper region of a display region of the display image, arranging and displaying an operative field image generated on the basis of the operative field image signal in a middle region that has a length equivalent to the upper region in a horizontal direction, and arranging and displaying user interface information used to control a control device in a region on a lower side of the upper region.

(20)
A control method by a control device, including:
acquiring an operative field image signal generated by a medical imaging device that images an operative field of a patient and a presented information signal generated by a device that includes an external device excluding the medical imaging device;

generating a display image on the basis of the operative field image signal and the presented information signal; and generating the display image by arranging and displaying presented information generated from the presented information signal in an upper region of a display region of the display image, arranging and displaying an operative field image generated on the basis of the operative field image signal in a middle region that has a length equivalent to the upper region in a horizontal direction, and arranging and displaying user interface information used to control a control device in a region on a lower side of the upper region.

REFERENCE SIGNS LIST

1 Medical display system
11 Microscope device
12 Control device
13 Monitoring device
14 Display device
15 Network
16 External server
81 Acquisition unit
82 Control unit
83 Display control unit

The invention claimed is:

1. A medical display system, comprising:
a control device including
  a Central processing unit (CPU) configured to:
    acquire an operative field image signal generated by a medical imaging device that images an operative field of a patient and a presented information signal generated by a device that includes an external device excluding the medical imaging device;
    generate a display image based on the operative field image signal and the presented information signal, wherein the display image is generated by display of:
      presented information, generated from the presented information signal, in an upper region of a display region of the display image,
      an operative field image, generated based on the operative field image signal, in a middle region that has a length equivalent to the upper region in a horizontal direction, and
      user interface information used to control the control device in a region on a lower side of the display region of the display image;
    specify a work concentration region in the operative field image on which a user line-of-sight is concentrated; and
    determine an arrangement position of information superimposed on the operative field image, based on the specified work concentration region.

2. The medical display system according to claim 1, wherein
the presented information includes at least monitoring information generated from a monitoring information signal acquired from a monitoring device that monitors biological information of the patient.

3. The medical display system according to claim 2, wherein
the CPU is further configured to arrange the presented information in a specific display form including a text or a graph.

4. The medical display system according to claim 2, wherein
the presented information includes information regarding surgical instruments.

5. The medical display system according to claim 2, wherein
the presented information includes information regarding a time.

6. The medical display system according to claim 2, wherein
the presented information includes information that changes in real time.

7. The medical display system according to claim 2, wherein
the CPU is configured to change a method for display of the presented information arranged in the upper region based on information regarding a user.

8. The medical display system according to claim 7, wherein
the information regarding the user includes information regarding a user's the user line-of-sight or information based on an operation or a behavior of the user.

9. The medical display system according to claim 1, wherein
the operative field image includes an image that changes in real time.

10. The medical display system according to claim 1, wherein
the region on the lower side is a lower region that has a length equivalent to the upper region in the horizontal direction, and
the CPU is further configured to arrange the user interface information in the lower region.

11. The medical display system according to claim 1, wherein
the region on the lower side is a lower region that has a length different from the upper region in the horizontal direction, and
the lower region includes a left portion region and a right portion region corresponding to at least one of regions at a left end or a right end of the middle region, and
the CPU is further configured to arrange the user interface information in the left portion region and right portion region.

12. The medical display system according to claim 1, wherein
the CPU is further configured to arrange one or a plurality of captured images, generated by another medical imaging device different from the medical imaging device, in a lower region on the lower side of the display region.

13. The medical display system according to claim 12, wherein
the CPU is further configured to:
  arrange a thumbnail image corresponding to a reference image that is a captured image for reference,
  align and arrange a plurality of reference images corresponding to the thumbnail image in a specific direction based on the thumbnail image is selected, and
  arrange the reference image obtained by an enlarging operation of a specific reference image based on the specific reference image is selected from among the plurality of reference images.

14. The medical display system according to claim 1, wherein
the CPU is further configured to arrange a direction indicator used to change a display range of the operative field image in the region on the lower side.

15. The medical display system according to claim 1, wherein
the CPU is further configured to determine the arrangement position so that an alert or information for reference is arranged in a region excluding the work concentration region.

16. The medical display system according to claim 1, wherein
the CPU is further configured to:
detect the user line-of-sight with respect to the middle region, and
execute a line-of-sight region corresponding processing operation regarding a line-of-sight region based on the detected user line-of-sight.

17. The medical display system according to claim 16, wherein
based on target exists in the line-of-sight region, the line-of-sight region corresponding processing operation includes a processing operation for selection of the target according to voice of a user, a processing operation to mark at a position indicated by the line-of-sight region according to the voice of the user, and a processing operation to focus on the target in the line-of-sight region.

18. A control device, comprising:
a Central processing unit (CPU) configured to:
acquire an operative field image signal generated by a medical imaging device that images an operative field of a patient and a presented information signal generated by a device that includes an external device excluding the medical imaging device;
generate a display image based on the operative field image signal and the presented information signal, wherein the display image is generated by display of:
presented information, generated from the presented information signal, in an upper region of a display region of the display image,
an operative field image, generated based on the operative field image signal, in a middle region that has a length equivalent to the upper region in a horizontal direction, and
user interface information used to control the control device in a region on a lower side of the display region of the display image;
specify a work concentration region in the operative field image on which a user line-of-sight is concentrated; and
determine an arrangement position of information superimposed on the operative field image, based on the specified work concentration region.

19. A control method by a control device, comprising:
acquiring an operative field image signal generated by a medical imaging device that images an operative field of a patient and a presented information signal generated by a device that includes an external device excluding the medical imaging device;
generating a display image based on the operative field image signal and the presented information signal, wherein the display image is generated by displaying:
presented information, generated from the presented information signal, in an upper region of a display region of the display image,
an operative field image, generated based on the operative field image signal, in a middle region that has a length equivalent to the upper region in a horizontal direction, and
user interface information used to control the control device in a region on a lower side of the display region of the display image;
specifying a work concentration region in the operative field image on which a user line-of-sight is concentrated; and
determining an arrangement position of information superimposed on the operative field image, based on the specified work concentration region.

* * * * *